US011390632B2

(12) United States Patent
Adam et al.

(10) Patent No.: US 11,390,632 B2
(45) Date of Patent: Jul. 19, 2022

(54) PROCESS FOR THE PREPARATION OF 7-(4,7-DIAZASPIRO[2.5]OCTAN-7-YL)-2-(2,8-DIMETHYLIMIDAZO[1,2-B]PYRIDAZIN-6-YL)PYRIDO[1,2-A]PYRIMIDIN-4-ONE DERIVATIVES

(71) Applicant: Hoffmann-La Roche Inc., Little Falls, NJ (US)

(72) Inventors: Jean-Michel Adam, Basel (CH); Serena Maria Fantasia, Basel (CH); Daniel Vincent Fishlock, Basel (CH); Fabienne Hoffmann-Emery, Basel (CH); Gerard Moine, Basel (CH); Christophe Pfleger, Basel (CH); Christian Moessner, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/824,212

(22) Filed: Mar. 19, 2020

(65) Prior Publication Data
US 2020/0216472 A1 Jul. 9, 2020

Related U.S. Application Data

(63) Continuation of application No. PCT/EP2018/075282, filed on Sep. 17, 2018.

(30) Foreign Application Priority Data

Sep. 22, 2017 (EP) ..................................... 17192711

(51) Int. Cl.
*C07D 519/00* (2006.01)
*B01J 23/44* (2006.01)
*B01J 23/755* (2006.01)

(52) U.S. Cl.
CPC ............ *C07D 519/00* (2013.01); *B01J 23/44* (2013.01); *B01J 23/755* (2013.01)

(58) Field of Classification Search
CPC ...................................................... C07D 519/00
See application file for complete search history.

(56) References Cited

U.S. PATENT DOCUMENTS

2015/0005289 A1* 1/2015 Qi ........................... A61P 21/00
514/210.21

FOREIGN PATENT DOCUMENTS

| WO | 2013/119916 A2 | 8/2013 |
| WO | 2015/173181 A1 | 11/2015 |
| WO | 2016/058501 A1 | 4/2016 |
| WO | 2017/080967 A1 | 5/2017 |
| WO | 2017/081111 A1 | 5/2017 |

OTHER PUBLICATIONS

Nudelman et al. Synthetic Communications, 28(3), 471-474 . (Year: 1998).*
English translation of WO2016/058501 A1, pp. 1-32.
International Preliminary Report on Patentability for PCT/EP2018/075282 dated Mar. 24, 2020.
International Search Report for PCT/EP2018/075282 dated Oct. 23, 2018.

* cited by examiner

*Primary Examiner* — Erich A Leeser
(74) *Attorney, Agent, or Firm* — Bradley E. Davis

(57) ABSTRACT

The present invention relates to a process for the preparation of 7-(4,7-diazaspiro[2.5]octan-7-yl)-2-(2,8-dimethylimidazo[1,2-b]pyridazin-6-yl)pyrido[1,2-a]pyrimidin-4-one derivatives useful as pharmaceutically active compounds.

26 Claims, No Drawings

PROCESS FOR THE PREPARATION OF 7-(4,7-DIAZASPIRO[2.5]OCTAN-7-YL)-2-(2,8-DIMETHYLIMIDAZO [1,2-B]PYRIDAZIN-6-YL)PYRIDO[1,2-A]PYRIMIDIN-4-ONE DERIVATIVES

CROSS REFERENCE TO RELATED APPLICATIONS

This application is a continuation of International Application No. PCT/EP2018/075282, filed Sep. 17, 2018, which claims benefit to European Patent Application No. 17192711.4, filed Sep. 22, 2017; all of which are incorporated by reference in their entirety.

FIELD OF THE INVENTION

The present invention relates to a process for the preparation 7-(4,7-diazaspiro[2.5]octan-7-yl)-2-(2,8-dimethylimidazo[1,2-b]pyridazin-6-yl)pyrido[1,2-a]pyrimidin-4-one useful as pharmaceutically active compounds.

In a first aspect, the present invention provides a process for the preparation of a compound of formula (I) or the HCl salt thereof:

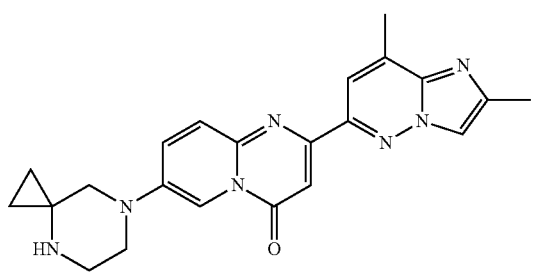

(I)

which comprises reacting compound of formula (II):

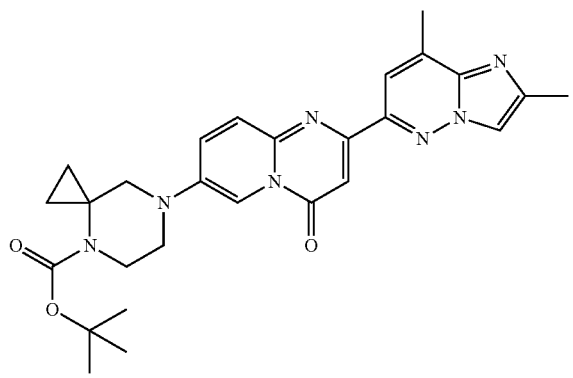

(II)

with a strong acid, in particular HCl.

The process according to the first aspect, wherein the HCl is made in situ in the presence of 1-propanol and acetyl chloride.

In particular, the preparation of compound of formula (I) is being carried out in a solvent such as an alcohol, an aqueous alcohol, ethyl-acetate, 1-propylacetate, toluene, acetonitrile, THF or dichloromethane. More preferably the preparation of compound of formula (I) is being carried out in the presence of 1-propanol and toluene.

In a particular embodiment, the present invention provides a process as described herein, wherein 3 to 15 equivalents, more particularly 4 to 8 equivalents, most particularly 5 equivalents of strong acid, in particular wherein the strong acid is HCl, with respect to compound of formula (II) is used.

In another embodiment, the present invention provides a process as described above for the preparation of compound of formula (I), wherein the reaction is carried out at a temperature between 20° C. to 100° C., particularly between 60° C. to 80° C., more particularly at 75° C.

The compound of formula (I) 7-(4,7-diazaspiro[2.5]octan-7-yl)-2-(2,8-dimethylimidazo[1,2-b]pyridazin-6-yl)pyrido[1,2-a]pyrimidin-4-one is a valuable pharmaceutical compound as described in WO2015173181.

Unless otherwise stated, the following terms used in the specification and claims have the meanings given below:

"$(C_1-C_8)$alkyl" refers to a branched or straight hydrocarbon chain, such as methyl, ethyl, n-propyl, isopropyl, n-butyl, isobutyl, sec-butyl and t-butyl, pentyl, hexyl, heptyl or octyl. "$(C_1-C_3)$alkyl" refers methyl, ethyl, n-propyl or isopropyl.

"alcohol" refers to a benzyl alcohol, aminoethanol or an $(C_{1-8})$alkyl (more particularly $(C_1-C_3)$alkyl) as defined above substituted by one or two hydroxy groups, more particularly substituted by one hydroxy group. Examples of alcohols include, but are not limited to, methanol, ethanol, isopropanol, 1-propanol, propylenglycol, 1-butanol, 2-butanol, t-butanol, benzyl alcohol, 2-aminoethanol and octanol. Particularly, alcohol refers to methanol, ethanol, 1-propanol or benzylalcohol, most particularly to 1-propanol.

"ambient conditions" refers to conditions as experienced in a standard laboratory, e.g. atmospheric pressure, air, ambient temperature between 18° C. and 28° C., humidity between 30% rH and 80% rH.

"base" refers to a chemical compound that deprotonates another compound when reacted with it. Suitable bases for use in accordance with this disclosure include but are not limited to, e.g., an organic base and basic alkali metal salts. In particular, an organic base includes nitrogen-containing heterocycle and tertiary amines. Examples of nitrogen-containing heterocycle include pyridine, imidazole and benzimidazole. In some embodiments, the tertiary amines include triethylamine, N-methylmorpholine and diisopropylethylamine. In some embodiments, the basic alkali metal salts include, e.g., sodium carbonate ($Na_2CO_3$), potassium carbonate ($K_2CO_3$), sodium bicarbonate ($NaHCO_3$), sodium hydroxide (NaOH), sodium and potassium alkoxides including, but not limited to, sodium and potassium t-butoxide, 1-propoxide, 2-propoxide, ethoxide, methoxide, and the like, sodium amide ($NaNH_2$), potassium amide ($KNH_2$), and the like.

"crystallization" and "recrystallization" may be used interchangeably; referring to a process wherein a chemical compound that is dissolved or suspended in a solvent system leads to a stable polymorph or crystalline form of a particular chemical compound. For example the crystallization steps can be done by forming a crystal with a solvent and an anti-solvent.

The terms "halo", "halogen" and "halide", which may be used interchangeably, refer to a substituent chloro, bromo, or iodo.

"strong acid" refers to an acid that dissociates completely in an aqueous solution with a pH≤2. The strong acids include, but are not limited to: sulphuric acid ($H_2SO_4$), hydrohalogenic acid (i.e. HX" wherein X" is I, Br, Cl or F), nitric acid (HNO$_3$), phosphoric acid (H$_3$PO$_4$) and combinations thereof. Particularly, the strong acid is hydrohalogenic acid, wherein X" is Br or Cl. Most particularly, the strong acid is HCl.

"Nickel catalyst" refers to catalysts comprising nickel or nickel oxides or mixtures thereof. Example of Nickel catalyst is Raney-nickel catalyst (Ra-Ni).

The term "optional" or "optionally" denotes that a subsequently described event or circumstance can but need not occur, and that the description includes instances where the event or circumstance occurs and instances in which it does not.

"palladium catalyst" refers to reagent which is a source of palladium zero (Pd(0)). Suitable sources of Pd(0) comprises but are not limited to palladium bis(dibenzylideneacetone) (Pd(dba)$_2$), bis(triphenylphosphine)palladium(II) dichloride (Pd(PPh$_3$)$_2$Cl$_2$), palladium acetate (Pd(OAc)$_2$), palladium chloride (PdCl$_2$), tetrakis (triphenyl-phosphino) palladium (Pd(PPh$_3$)$_4$), 1,2 bis(diphenylphosphino) ethane palladium (Pd(dppe)$_2$), 1,3-bis(diphenylphosphino)-propane palladium (Pd(dppp)$_2$), dichloro-1,3-bis(diphenylphosphino)-propane palladium (PdCl$_2$(dppp)), 1,4-bis(diphenyl-phosphino) butane palladium, 1,1-bis (diphenylphosphine)-ferrocen dichloro palladium (PdCl$_2$(dppf)), palladium on carbon, Pd(OH)$_2$ on carbon, tris(dibenzylideneacetone)dipalladium(0) (Pd$_2$(dba)$_3$), bis(acetonitrile)-palladium(II) dichloride (PdCl$_2$(CH$_3$CN)$_2$), cyclopentadienyl allyl palladium, allylpalladium(II) chloride dimer (Pd(allyl)Cl)$_2$), (2-butenyl)chloropalladium dimer, (2-methylallyl) palladium(II) chloride dimer, palladium(1-phenylallyl)chloride dimer, di-µ-chlorobis[2'-(amino-N)[1,1'-biphenyl]-2-yl-C] dipalladium(II), di-µ-chlorobis[2-[(dimethylamino)methyl]phenyl-C,N]dipalladium(II) or dichloro[9,9-dimethyl-4,5-bis(diphenylphosphino)xanthene]palladium (Pd(XantPhos)Cl$_2$). In particular the palladium catalyst refers to Pd(OAc)$_2$, Pd(PPh$_3$)$_4$, Pd(PPh$_3$)$_2$Cl$_{12}$, Pd$_2$(dba)$_3$, (Pd(XantPhos)Cl$_2$) or PdCl$_2$(dppf). More particularly the palladium catalyst is Pd(OAc)$_2$, Pd$_2$(dba)$_3$, (Pd(XantPhos)Cl$_2$) or PdCl$_2$(dppf).

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

"Transition metal hydrogenation catalyst" refers to a transition metal hydrogenation catalyst, which acts in a different phase than the substrate. Especially the transition metal hydrogenation catalyst is in the solid phase. In particular while the transition metal hydrogenation catalyst is in the solid phase, the reactants are in the liquid phase. The transition metal hydrogenation catalyst contains a transition metal, which forms one or more stable ions, which have incompletely filled d orbitals (i.e. Pd, Pt, Rh, Au, Ni, Co, Ru, Ir, V, Fe) in particular noble metal, such as Pd, Pt, Rh or Au. In these catalysts the transition metal is in particular "supported", which means that the catalyst is dispersed on a second material that enhances the effectiveness. The "support" can be merely a surface on which the metal is spread to increase the surface area. The supports are porous materials with a high surface area, most commonly alumina or various kinds of carbon. Further examples of supports include, but are not limited to, silicon dioxide, titanium dioxide, calcium carbonate, barium sulfate, diatomaceous earth and clay. The metal itself can also act as a support, if no other support is present. More specifically the term "Transition metal hydrogenation catalyst" includes but is not limited to, a Raney catalyst (e.g. Ra-Ni, Ra-Co,) Pd/C, Pd(OH)$_2$/C, Au/TiO$_2$, Rh/C, Ru/Al$_2$O$_3$, Ir/CaCO$_3$, Pt—V/C or Pt/C, in particular Pt—V/C.

"Tertiary amine" refers to an amine of formula R$^a$N(R$^b$)R$^c$ wherein R$^a$, R$^b$ and R$^c$ independently are selected from (C$_1$-C$_6$)alkyl or phenyl. Representative examples include, but are not limited to, triethylamine, tributylamine, di-ethyl-methylamine, dimethyl-ethylamine, di-isopropylethylamine, N,N-dimethylaniline and methylethylbutyl amine. Preferably, the tertiary amine is chosen from triethylamine or di-isopropylethylamine. The most preferred tertiary amine is triethylamine.

The term "treating", "contacting" or "reacting" used interchangeably refers to adding, bringing together or mixing two or more chemical substances (referred usually as reagents or reactants), more particularly under appropriate conditions, to produce the indicated and/or the desired product. It should be appreciated that the reaction which produces the indicated and/or the desired product may not necessarily result directly from the combination of two or more reagents which were initially added, i.e., there may be one or more intermediates which are produced in the mixture which ultimately leads to the formation of the indicated and/or the desired product."

In another aspect (aspect 2), the present invention provides a process for the preparation of a compound of formula (II)

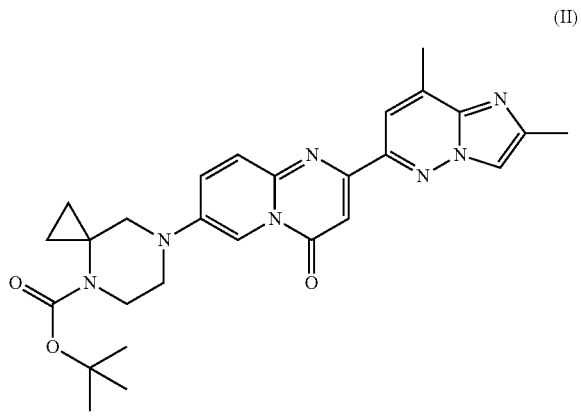 [SMILES: Cc1cn2nc(-c3cc(=O)n4cc(N5CCN(C(=O)OC(C)(C)C)C6(CC6)C5)ccc4n3)cc(C)c2n1]

which comprises reacting a compound of formula (III)

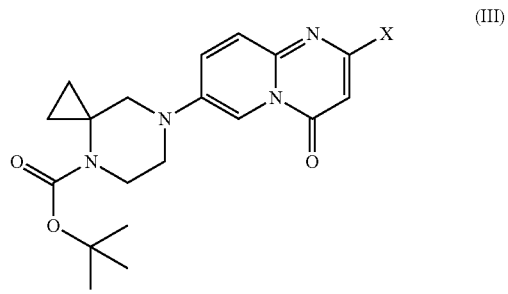

wherein X is an alkyl or aryl sulfonate (such as pTolSO$_3$—, CH$_3$SO$_3$—, phenyl-SO$_3$—), fluorinated alkyl or aryl sulfonates (such as CF$_3$SO$_3$—, nonaflate), or a halide (such as Cl, Br, or I), with a compound of formula (III'), (III$_a$') or (III$_b$'), in particular with a compound of formula (III')

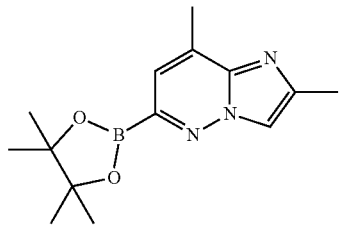
(III')

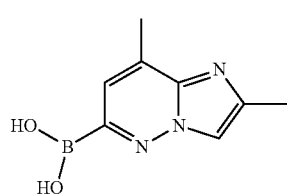
(III$_a$')

(III$_b$')

in the presence of a palladium catalyst or nickel catalyst, in particular in presence of a palladium catalyst.

In a particular embodiment of aspect 2, the present invention provides a process for the preparation of a compound of formula (II)

(II)

which comprises reacting a compound of formula (III)

(III)

wherein X is an alkyl or aryl sulfonate (such as pTolSO$_3$—, CH$_3$SO$_3$—, phenyl-SO$_3$—), fluorinated alkyl or aryl sulfonates (such as CF$_3$SO$_3$—, nonaflate), with a compound of formula (III')

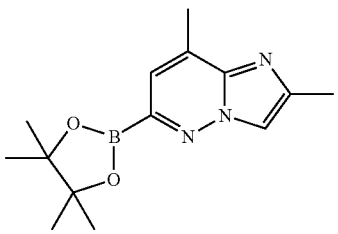
(III')

in the presence of a palladium catalyst or nickel catalyst, in particular in presence of a palladium catalyst.

In a more particular embodiment of aspect 2, the present invention provides a process for the preparation of a compound of formula (II)

(II)

which comprises reacting a compound of formula (III$_a$)

(III$_a$)

with a compound of formula (III′)

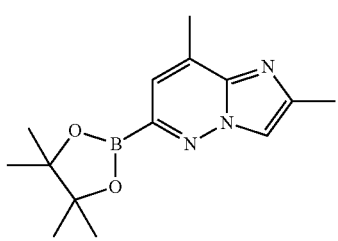
(III′)

in the presence of a palladium catalyst or nickel catalyst, in particular in presence of a palladium catalyst.

In particular, the process as described herein (i.e. aspect 2) which further comprises a base, particularly wherein the base is $Na_2CO_3$, $K_2CO_3$, $Cs_2CO_3$, KOAc or KOtBu more particularly wherein the base is $K_2CO_3$.

In yet another aspect (aspect 3), the present invention provides a process for the preparation of a compound of formula (II)

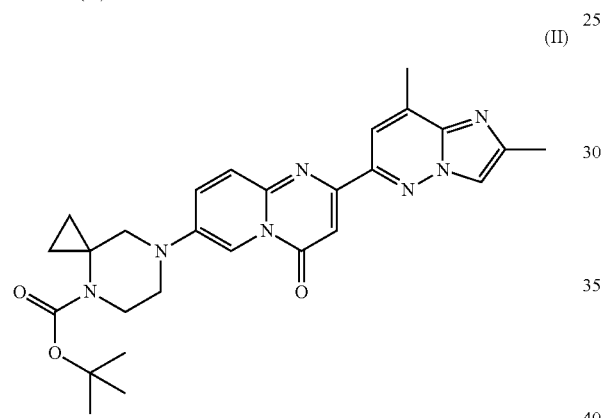
(II)

which comprises a) reacting a compound of formula (III″)

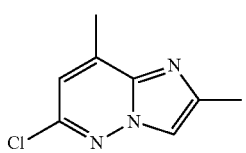
(III″)

with bis(pinacolato)diboron to obtain a compound of formula (III′):

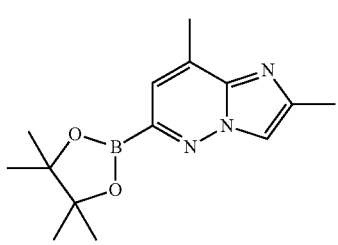
(III′)

b) reacting a compound of formula (III)

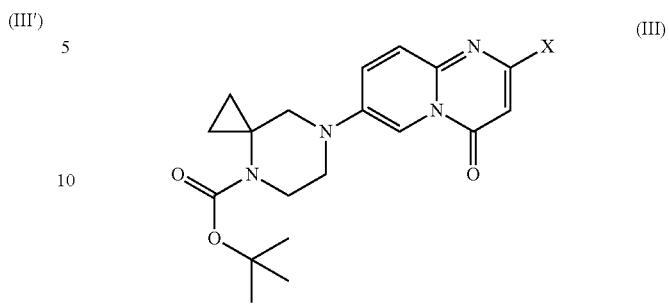
(III)

wherein X is an alkyl or aryl sulfonate (such as $pTolSO_3$—, $CH_3SO_3$—, phenyl-$SO_3$—), fluorinated alkyl or aryl sulfonates (such as $CF_3SO_3$—, nonaflate), or a halide (such as Cl, Br, or I) with a compound of formula (III′), (III$_a$′) or (III$_b$′), in particular with a compound of formula (III′),

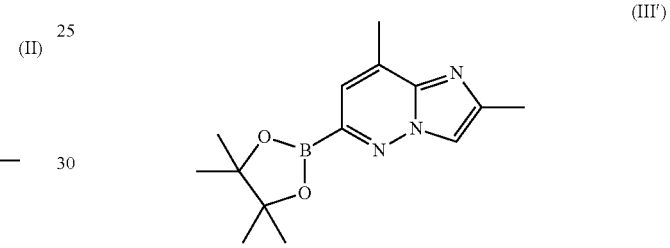
(III′)

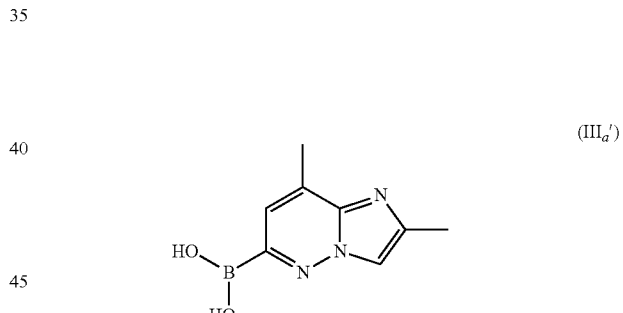
(III$_a$′)

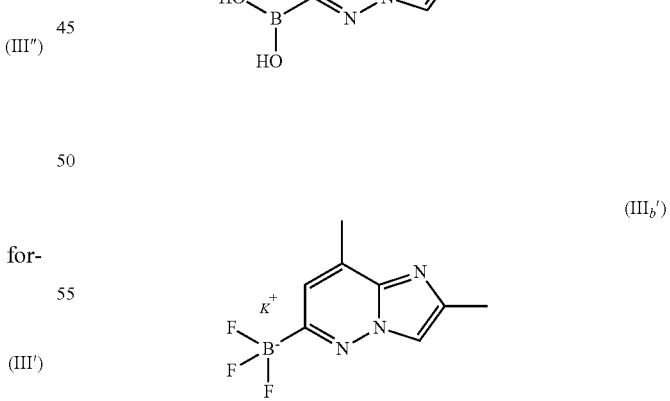
(III$_b$′)

in the presence of a palladium catalyst or nickel catalyst, in particular in presence of a palladium catalyst, to obtain a compound of formula (II).

In a particular embodiment of aspect 3, the present invention provides a process for the preparation of a compound of formula (II)

(II)

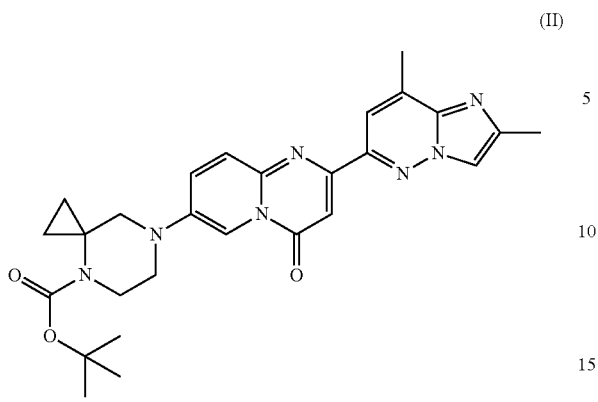

which comprises
a) reacting a compound of formula (III″)

(III″)

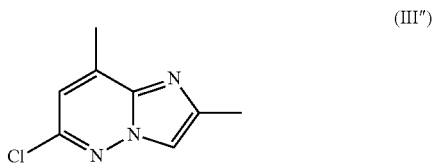

with bis(pinacolato)diboron to obtain a compound of formula (III′):

(III′)

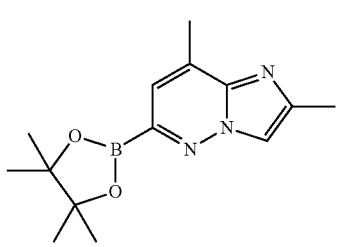

b) reacting a compound of formula (III)

(III)

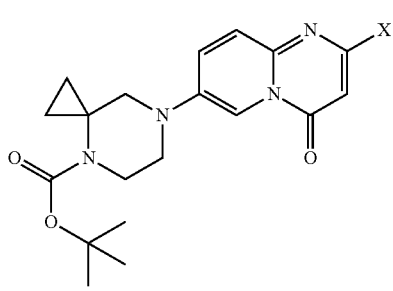

wherein X is an alkyl or aryl sulfonate (such as pTolSO₃—, CH₃SO₃—, phenyl-SO₃—), fluorinated alkyl or aryl sulfonates (such as CF₃SO₃—, nonaflate) with a compound of formula (III′)

(III′)

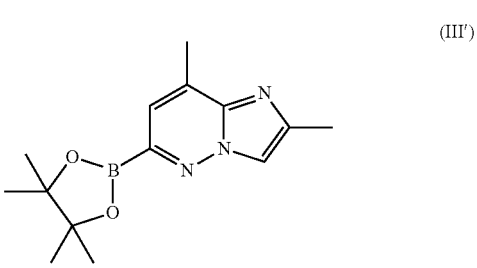

in the presence of a palladium catalyst or nickel catalyst, in particular in presence of a palladium catalyst, to obtain a compound of formula (II).

In a more particular embodiment of aspect 3, the present invention provides a process for the preparation of a compound of formula (II)

(II)

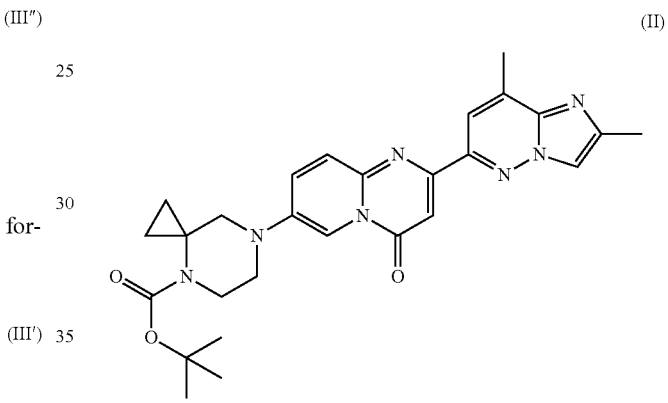

which comprises
a) reacting a compound of formula (III″)

(III″)

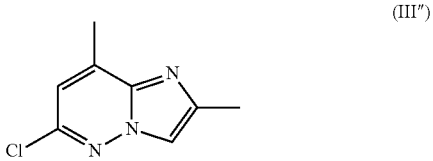

with bis(pinacolato)diboron to obtain a compound of formula (III′):

(III′)

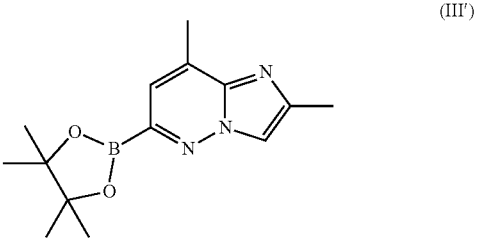

b) reacting a compound of formula (III$_a$)

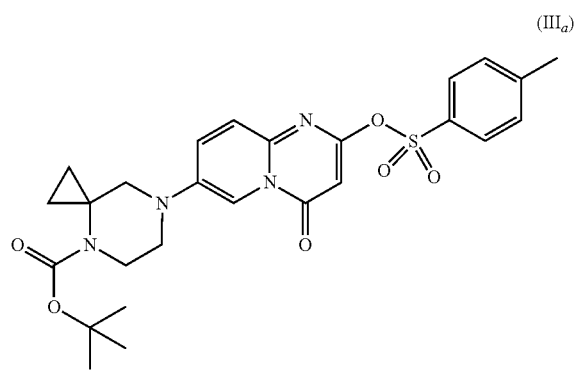 [SMILES: Cc1ccc(S(=O)(=O)Oc2cc(=O)n3cc(N4CCN(C(=O)OC(C)(C)C)C5(CC5)C4)ccc3n2)cc1]

with a compound of formula (III')

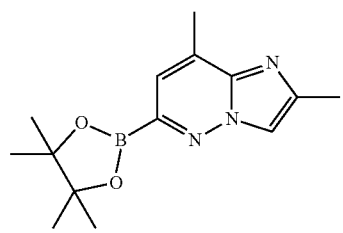

in the presence of a palladium catalyst or nickel catalyst, in particular in presence of a palladium catalyst, to obtain a compound of formula (II).

In particular the invention provides a process as described above, wherein the reaction of compound of formulae (III) or (III$_a$) with compound of formulae (III'), (III$_a$') or (III$_b$'), in particular with a compound of formula (III') in the presence of palladium catalyst or nickel catalyst, in particular in presence of a palladium catalyst as defined herein, is carried out in presence of a base, particularly wherein the base is Na$_2$CO$_3$, K$_2$CO$_3$, Cs$_2$CO$_3$, KOAc or KOtBu more particularly wherein the base is K$_2$CO$_3$.

In a particular embodiment, the present invention provides the process herein described wherein steps a) and b) are telescoped.

In yet another aspect (aspect 4), the present invention provides a process for the preparation of a compound of formula (III)

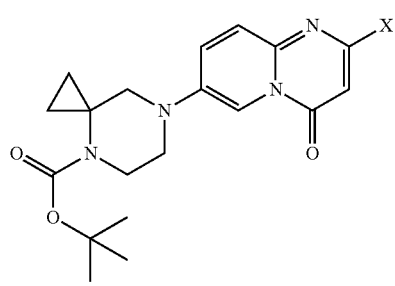

wherein X is an alkyl or aryl sulfonate (such as pTolSO$_3$—, CH$_3$SO$_3$—, phenyl-SO$_3$—), fluorinated alkyl or aryl sulfonates (such as CF$_3$SO$_3$—, nonaflate), or a halide (such as Cl, Br, or I), which comprises reacting a compound of formula (IV)

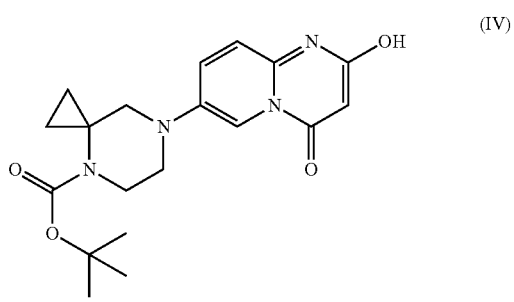 [SMILES: CC(C)(C)OC(=O)N1CCN(c2ccc3nc(O)cc(=O)n3c2)CC12CC2]

with tosyl chloride when X is pTol-SO$_3$—, methanesulfonyl chloride when X is CH$_3$SO$_3$—, triflyl chloride when X is CF$_3$SO$_3$— or phenylsulfonylchloride when X is phenyl-SO$_3$—, and in the presence of a base, in particular wherein the base is an organic base or basic alkali metal salts, more particularly wherein the base is nitrogen-containing heterocycle, tertiary amine or basic alkali metal salts, most particularly wherein the base is a tertiary amine;

with POCl$_3$ when X is Cl;

with POBr$_3$ when X is Br; or with, Ph$_3$PI$_2$ or POCl$_3$ followed by NaI or CuI, when X is I.

In a particular embodiment of aspect 4, the present invention provides a process for the preparation of a compound of formula (III)

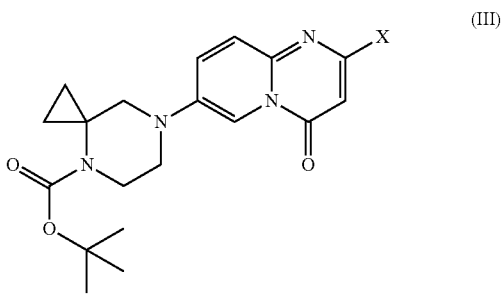

wherein X is an alkyl or aryl sulfonate (such as pTolSO$_3$—, CH$_3$SO$_3$—, phenyl-SO$_3$—), fluorinated alkyl or aryl sulfonates (such as CF$_3$SO$_3$—, nonaflate), which comprises reacting a compound of formula (IV)

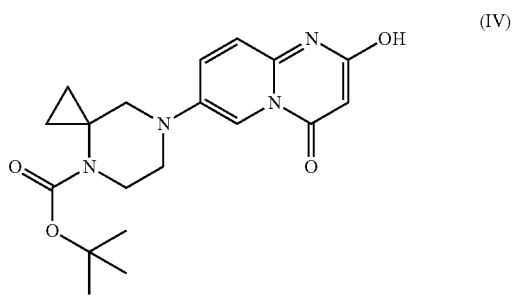 [SMILES: CC(C)(C)OC(=O)N1CCN(c2ccc3nc(O)cc(=O)n3c2)CC12CC2]

with tosyl chloride, methanesulfonyl chloride, phenyl sulfonylchloride or triflyl chloride respectively and in the presence of a base, in particular wherein the base is an organic base or basic alkali metal salts, more particularly wherein the base is nitrogen-containing heterocycle, tertiary amine or basic alkali metal salts, most particularly wherein the base is a tertiary amine.

In a more particular embodiment of aspect 4, the present invention provides a process for the preparation of a compound of formula (III$_a$)

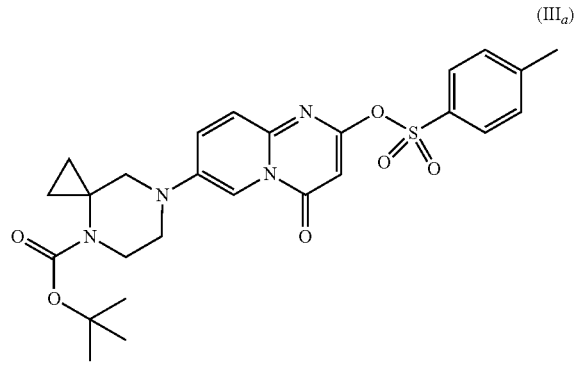 [SMILES: Cc1ccc(S(=O)(=O)Oc2cc(=O)n3cc(N4CCN(C(=O)OC(C)(C)C)C5(CC5)C4)ccc3n2)cc1]

(III$_a$)

which comprises reacting a compound of formula (IV)

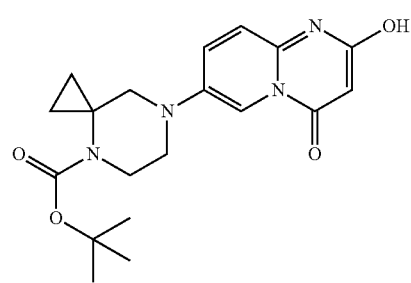

(IV)

with tosyl chloride and in the presence of a base, in particular wherein the base is an organic base or basic alkali metal salts, more particularly wherein the base is nitrogen-containing heterocycle, tertiary amine or basic alkali metal salts, most particularly wherein the base is a tertiary amine.

In yet another aspect (aspect 5), the present invention provides a process for the preparation of a compound of formula (IV)

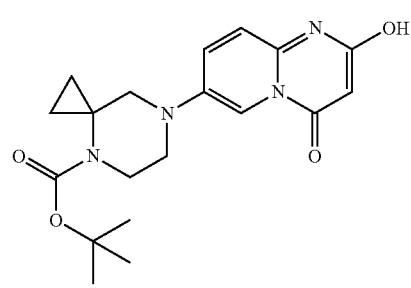

(IV)

which comprises reacting a compound of formula (V)

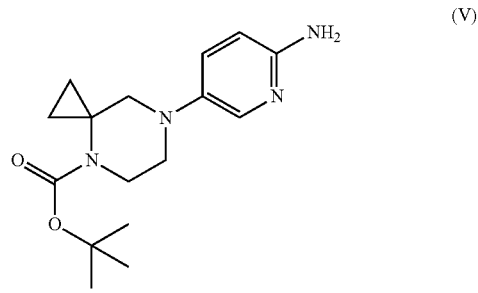 [SMILES: CC(C)(C)OC(=O)N1CCN(c2ccc(N)nc2)CC12CC2]

(V)

with di-tert-butyl malonate.

In yet another aspect (aspect 6), the present invention provides a process for the preparation of a compound of formula (IV)

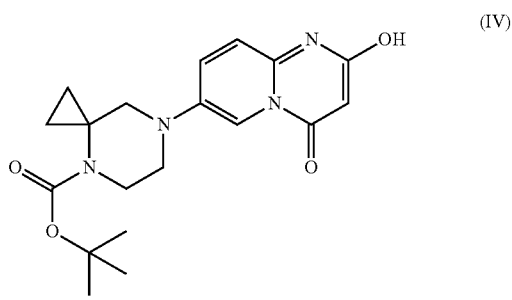 [SMILES: CC(C)(C)OC(=O)N1CCN(c2ccc3nc(O)cc(=O)n3c2)CC12CC2]

(IV)

which comprises:
a) reduction of a compound of formula (VI)

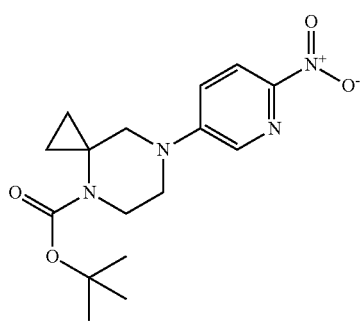

(VI)

to a compound of formula (V)

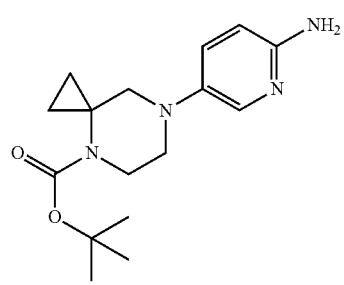

(V)

b) reacting a compound of formula (V) with di-tert-butyl malonate to obtain a compound of formula (IV).

In a more particular embodiment (aspect 7), the present invention provides a process for the preparation of a compound of formula (IV)

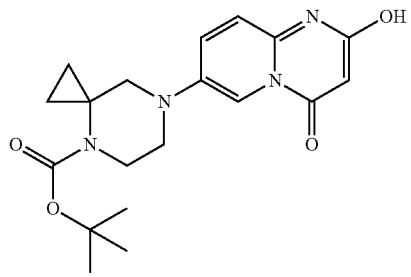
(IV)

which comprises:
a) reacting a compound of formula (VI)

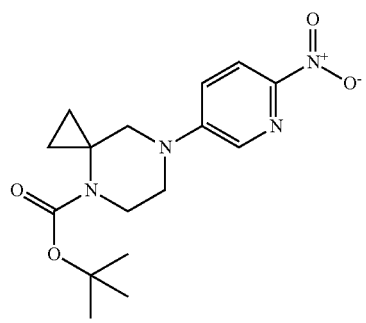
(VI)

with a transition metal hydrogenation catalyst to obtain a compound of formula (V)

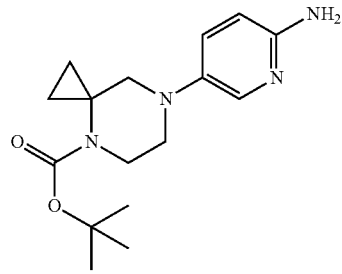
(V)

b) reacting a compound of formula (V) with di-tert-butyl malonate to obtain a compound of formula (IV).

In particular, the process for the preparation (i.e aspects 5 to 7) of a compound of formula (IV) which comprises reacting a compound of formula (V) with di-tert-butyl malonate, is carried out in the presence of xylene, dichlorobenzene, toluene or anisole, in particular in the presence of anisole.

In more particular, the preparation of compound of formula (IV), wherein the transition metal hydrogenation catalyst is Raney catalyst (e.g. Ra-Ni, Ra-Co,) Pd/C, Pd(OH)$_2$/C, Au/TiO$_2$, Rh/C, Ru/Al$_2$O$_3$, Ir/CaCO$_3$, Pt—V/C or Pt/C or combination thereof, in particular Pt—V/C, more particularly Pt 1% and V 2% on activated carbon.

In a particular embodiment, the present invention provides the process herein described wherein steps a) and b) are telescoped.

In another embodiment (aspect 8) the present application discloses the preparation of a compound of formula (VI)

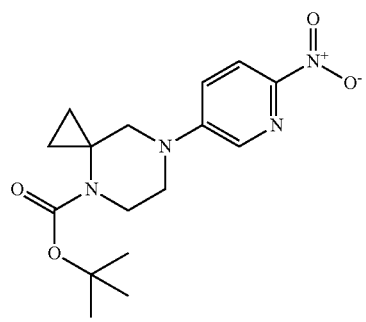
(VI)

which comprises reacting a compound of formula (VII)

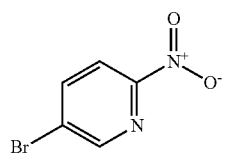
(VII)

with a compound of formula (VIII)

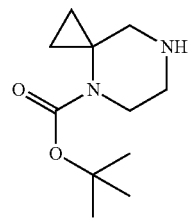
(VIII)

or a salt thereof (in particular the oxalate salt), more particularly wherein salt of the compound of formula (VIII) is tert-butyl 4,7-diazaspiro[2.5]octane-4-carboxylate oxalate salt.

In particular, the process for the preparation of a compound of formula (VI) which comprises reacting a compound of formula (VII) with a compound of formula (VIII), in the presence of lithium chloride, dimethyl sulfoxide and a base such as tetramethylguanidine, triethylamine, diisopropylethylamine or 1,8-diazabicyclo[5.4.0]undec-7-ene (DBU), most particular with tetramethylguanidine.

In a further embodiment the present application discloses the preparation of a compound of formula (V) in accordance to scheme 1.

Scheme 1

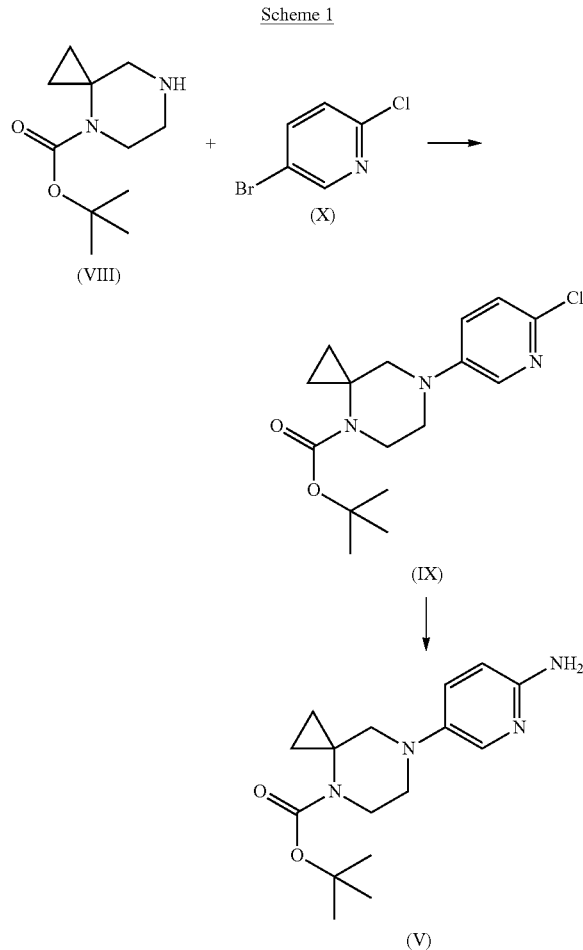

In particular, compound of formula (IX) can be prepared by reacting a compound of formula (X) with a compound of formula (VIII), in the presence of a catalyst (such as but not limited to Pd(PPh$_3$)$_4$, PdCl$_2$, Pd(OAc)$_2$, Pd$_2$(dba)$_3$, Pd(PPh$_3$)$_2$Cl$_2$, PdCl$_2$(dppf), PdCl$_2$(dppf).CH$_2$Cl$_2$, PdCl$_2$(dppp), PdCl$_2$(CH$_3$CN), Cyclopentadienyl allyl palladium, allylpalladium(II) chloride dimer (Pd(allyl)Cl)$_2$, (2-Butenyl) chloropalladium dimer, (2-Methylallyl) palladium(II) chloride dimer, palladium(1-phenylallyl)chloride dimer, chlorobis[2'-(amino-N)[1,1'-biphenyl]-2-yl-C]dipalladium(II), Di-μ-chlorobis[2-[(dimethylamino)methyl]phenyl-C,N]dipalladium(II), dichloro[9,9-dimethyl-4,5-bis(diphenylphosphino)xanthene]palladium (Pd(XantPhos)Cl$_2$), [Pd(allyl)(t-BuBrettPhos)]OTf, [Pd(crotyl)(tBuBrettPhos)]OTf, [Pd(cinnamyl)(tBuBrettPhos)]OTf in particular in the presence of dichloro[9,9-dimethyl-4,5-bis(diphenylphosphino)xanthene]palladium); and a base (such as Na$_2$CO$_3$, K$_2$CO$_3$, Cs$_2$CO$_3$, KOtBu, NaOtBu ((CH$_3$)$_3$CONa) or KOAc; in particular KOtBu), in particular in 2-methyltetrahydrofurane, THF or dioxane, more particularly in 2-methyltetrahydrofurane. Compound (V) can be prepared by reacting compound (IX) with ammonia (NH$_3$) in the presence of a catalyst such as Pd(PPh$_3$)$_4$, PdCl$_2$, Pd(OAc)$_2$, Pd$_2$(dba)$_3$, Pd(PPh$_3$)$_2$Cl$_{12}$, PdCl$_2$(dppf), PdCl$_{12}$(dppf).CH$_2$Cl$_2$, PdCl$_2$(dppp), PdCl$_2$(CH$_3$CN), Cyclopentadienyl allyl palladium, allylpalladium(II) chloride dimer (Pd(allyl)Cl)$_2$ (2-Butenyl) chloropalladium dimer, (2-Methylallyl) palladium(II) chloride dimer, palladium(1-phenylallyl)chloride dimer, chlorobis[2'-(amino-N)[1,1'-biphenyl]-2-yl-C]dipalladium(II), Di-μ-chlorobis[2-[(dimethylamino)methyl]phenyl-C,N]dipalladium(II), in particular in the presence of Pd$_2$(dba)$_3$, a base (such as Na$_2$CO$_3$, K$_2$CO$_3$, Cs$_2$CO$_3$, KOtBu, NaOtBu ((CH$_3$)$_3$CONa) or KOAc; in particular KOtBu) and t-Bu Brett Phos.

Preferably this step is carried out in dioxane.

Catalysts [Pd(allyl)(tBuBrettPhos)]OTf, [Pd(crotyl)(tBuBrettPhos)]OTf and [Pd(cinnamyl)(tBuBrettPhos)]OTf can be prepared in accordance with the compounds 8A, 8B and 8C respectively on page 6804 of A. J. DeAngelis, J. Org. Chem, 80, 6794-6813.

Compound of formula (V) can be also prepared in accordance to scheme 2.

Scheme 2

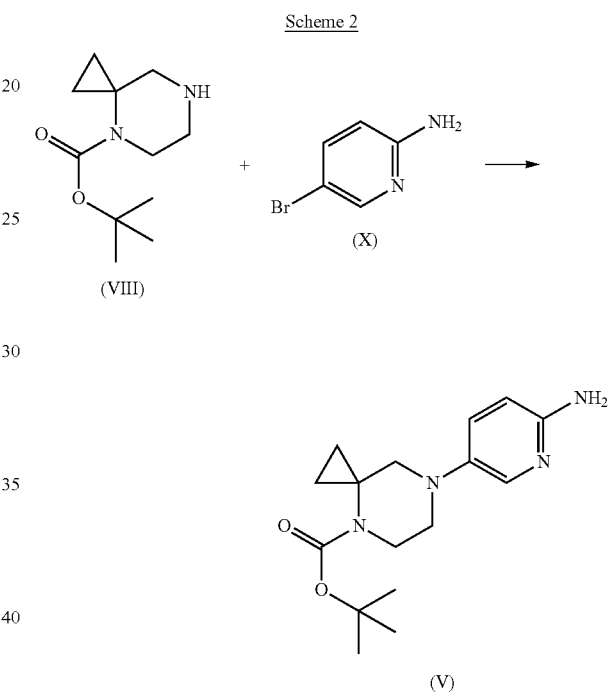

In particular, compound of formula (V) can be prepared by reacting a compound of formula (X) with a compound of formula (VIII), in the presence of a catalyst (such as Pd(PPh$_3$)$_4$, Pd(OAc)$_2$, Pd$_2$(dba)$_3$, PdCl$_2$, PdCl$_2$(dppf), PdCl$_2$(dppf).CH$_2$Cl$_2$, PdCl$_2$(dppp), allylpalladium(II) chloride dimer (Pd(allyl)Cl)$_2$ (2-butenyl) chloropalladium dimer, (2-methylallyl)palladium(II) chloride dimer, palladium(1-phenylallyl)chloride dimer, di-μ-chlorobis[2'-(amino-N)[1,1'-biphenyl]-2-yl-C]dipalladium(II), di-μ-chlorobis[2-[(dimethylamino)methyl]phenyl-C,N]dipalladium(II), in particular in the presence of allylpalladium(II) chloride dimer (Pd(allyl)Cl)$_2$ or palladium(1-phenylallyl)chloride dimer; and a ligand (such as 2-dicyclohexylphosphino-2'-(N,N-dimethylamino)biphenyl (DavePhos) or 2-di-tert-butylphosphino-2'-(N,N-dimethylamino)biphenyl (tBuDavePhos), in particular: tBuDavePhos) and a base (such as Na$_2$CO$_3$, K$_2$CO$_3$, Cs$_2$CO$_3$, KOtBu, NaOtBu ((CH$_3$)$_3$CONa), KOAc or lithium-bis(trimethylsilyl)amid; in particular lithium-bis(trimethylsilyl)amid), in particular in tetrahydrofuran.

In another embodiment, the present invention provides a compound of formula (II):

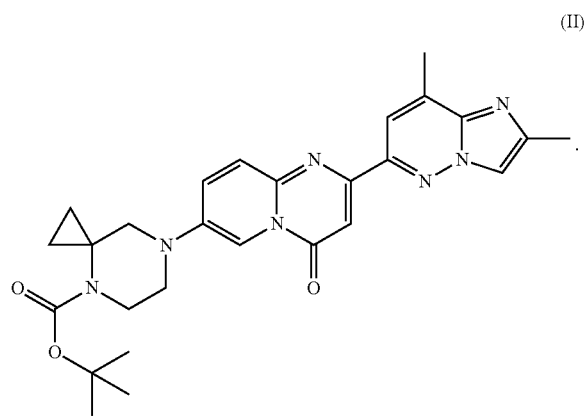 [SMILES: Cc1cn2nc(-c3cc(=O)n4cc(N5CCN(C(=O)OC(C)(C)C)C6(CC6)C5)ccc4n3)cc(C)c2n1]
(II)

In another embodiment, the present invention provides a compound of formula (III):

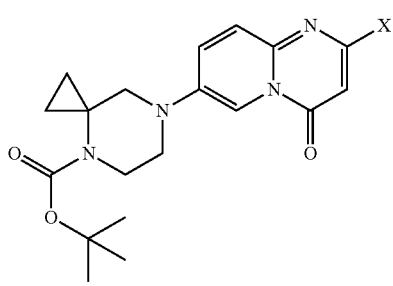
(III)

wherein X is an alkyl or aryl sulfonate (such as pTolSO₃—, CH₃SO₃—, phenyl-SO₃—), fluorinated alkyl or aryl sulfonates (such as CF₃SO₃—, nonaflate), or a halide (such as Cl, Br, or I).

In yet another embodiment, the present invention provides a compound of formula (III):

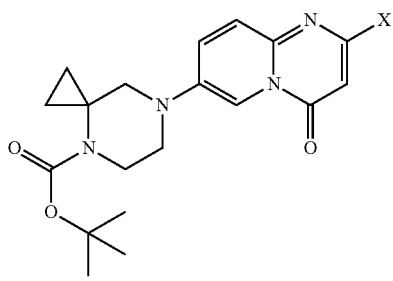
(III)

wherein X is an alkyl or aryl sulfonate (such as pTolSO₃—, CH₃SO₃—, phenyl-SO₃—), fluorinated alkyl or aryl sulfonates (such as CF₃SO₃—, nonaflate).

In another embodiment, the present invention provides a compound of formula (IIIa):

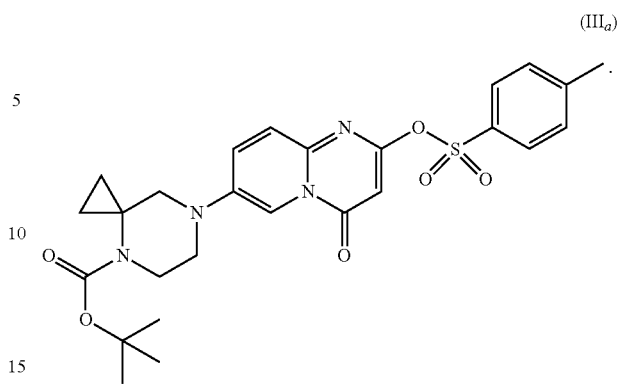
(IIIa)

In another embodiment, the present invention provides a compound of formula (IV):

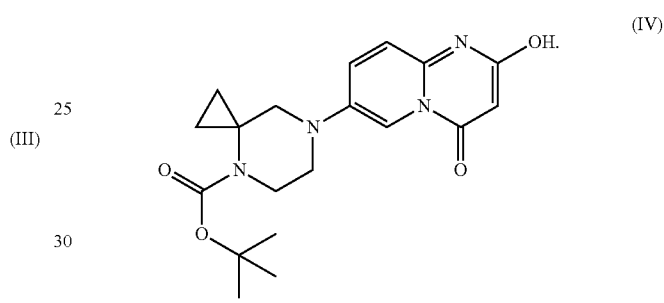
(IV)

The present invention takes place in the presence of an organic solvent such as an ether like solvent (e.g. tetrahydrofuran, diisopropyl ether, t-butylmethyl ether, cyclopentyl-methyl-ether or dibutyl ether), chlorinated solvents (e.g. dichloromethane, chloroform) or aromatic solvent (e.g. anisole, toluene or t-butyl-benzene). In particular, the solvent to be used for the preparation of a compound of formula (I) according to aspect 1 is toluene.

The reactions are performed in particular under an inert gas atmosphere, more particularly under argon or nitrogen.

In a further embodiment the present invention provides a process for the preparation of 7-(4,7-diazaspiro[2.5]octan-7-yl)-2-(2,8-dimethylimidazo[1,2-b]pyridazin-6-yl)pyrido[1,2-a]pyrimidin-4-one comprising the formation of a compound of formula (I) obtained by any of the processes and conditions mentioned previously.

In another embodiment (aspect 9), the present invention provides a process for the preparation of a compound of formula (I) or the HCl salt thereof:

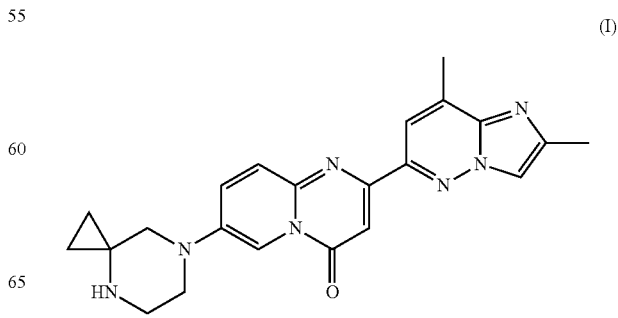
(I)

which comprises:
a) reacting a compound of formula (III)

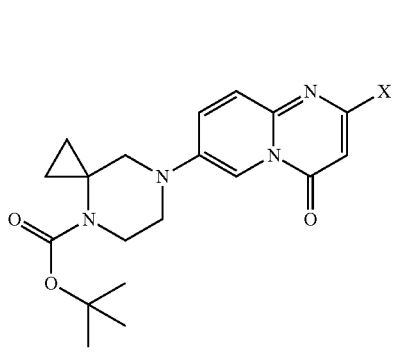

(III)

wherein X is an alkyl or aryl sulfonate (such as pTolSO$_3$—, CF$_3$SO$_3$—, phenyl-SO$_3$—), fluorinated alkyl or aryl sulfonates (such as CH$_3$SO$_3$—, nonaflate), or a halide (such as Cl, Br, or I), with a compound of formula (III'), (III$_a$') or (III$_b$'), in particular with a compound of formula (III')

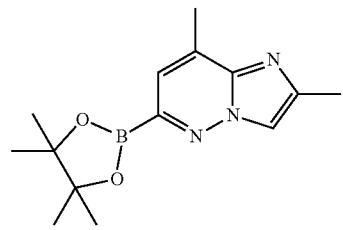

(III')

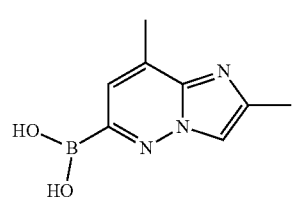

(III$_a$')

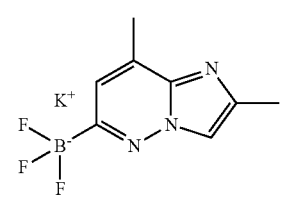

(III$_b$')

in the presence of a palladium catalyst or nickel catalyst, in particular in presence of a palladium catalyst, optionally in presence of a base, as previously described, to obtain a compound of formula (II):

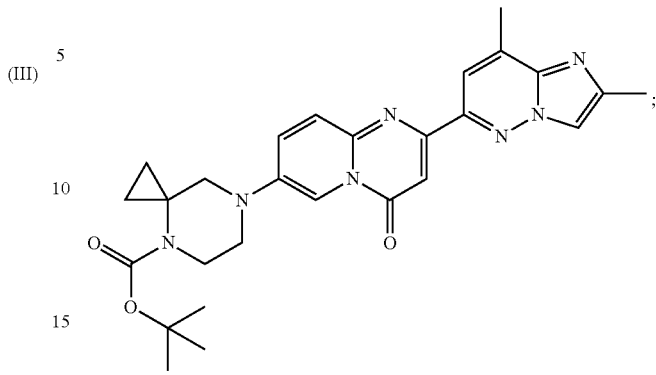

(II)

b) reacting said compound of formula (II) with a strong acid as previously described.

In a particular embodiment of aspect 9, the present invention provides a process for the preparation of a compound of formula (I) or the HCl salt thereof:

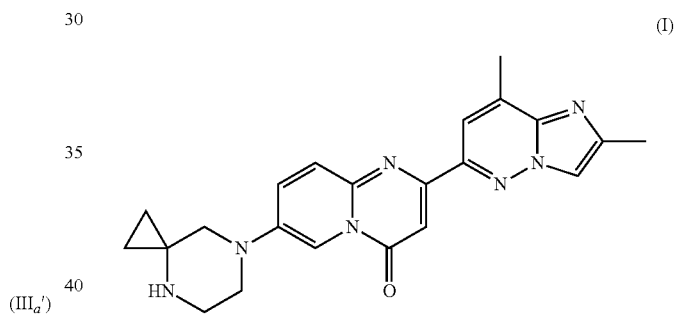

(I)

which comprises:
a) reacting a compound of formula (III)

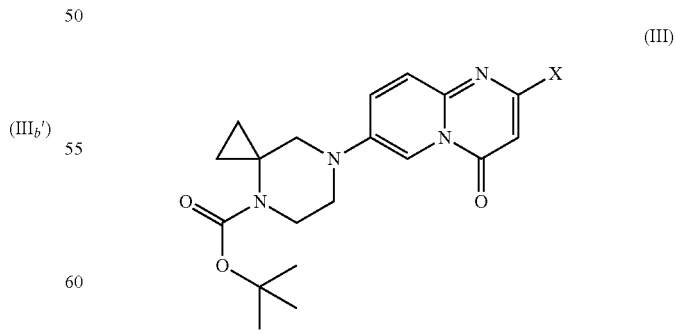

(III)

wherein X is an alkyl or aryl sulfonate (such as pTolSO$_3$—, CH$_3$SO$_3$—, phenyl-SO$_3$—), fluorinated alkyl or aryl sulfonates (such as CF$_3$SO$_3$—, nonaflate), with a compound of formula (III')

(III')

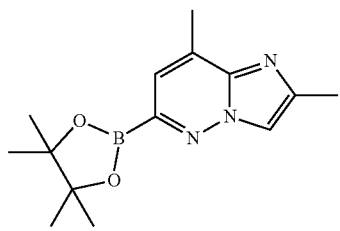

in the presence of a palladium catalyst or nickel catalyst, in particular in presence of a palladium catalyst, optionally in presence of a base, as previously described, to obtain a compound of formula (II):

(II)

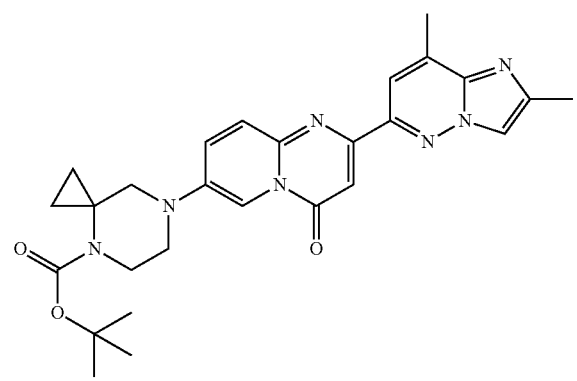

;

b) reacting said compound of formula (II) with a strong acid as previously described.

In a more particular embodiment of aspect 9, the present invention provides a process for the preparation of a compound of formula (I) or the HCl salt thereof:

(I)

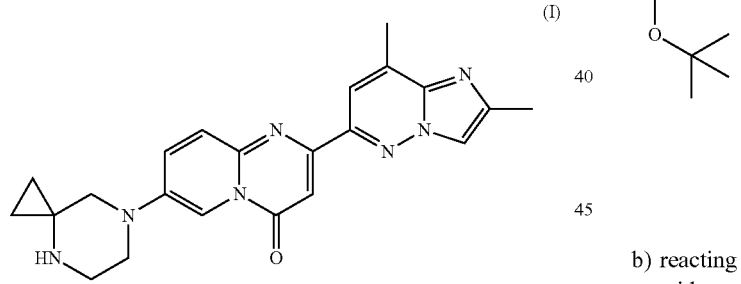

which comprises:
a) reacting a compound of formula (III$_a$)

(III$_a$)

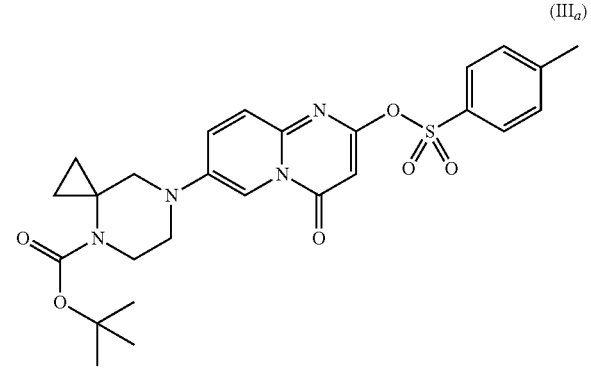 [SMILES: Cc1ccc(S(=O)(=O)Oc2cc(=O)n3cc(N4CCN(C(=O)OC(C)(C)C)C5(CC5)C4)ccc3n2)cc1]

with a compound of formula (III')

(III')

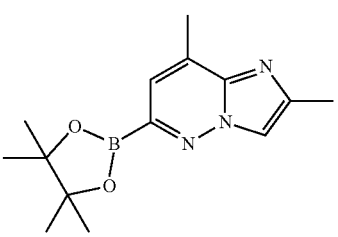

in the presence of a palladium catalyst or nickel catalyst, in particular in presence of a palladium catalyst, optionally in presence of a base, as previously described, to obtain a compound of formula (II):

(II)

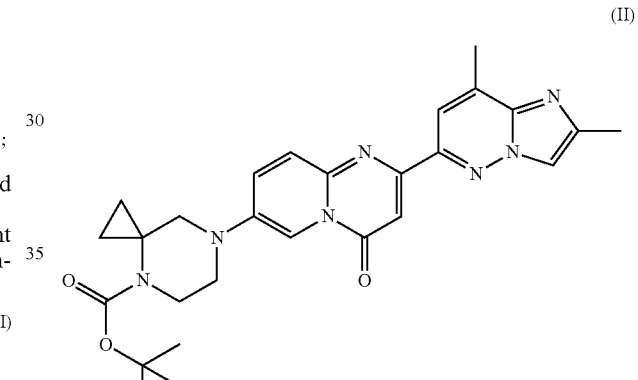

;

b) reacting said compound of formula (II) with a strong acid as previously described.

In another embodiment (aspect 10), the present invention provides a process for the preparation of a compound of formula (I) or the HCl salt thereof:

(I)

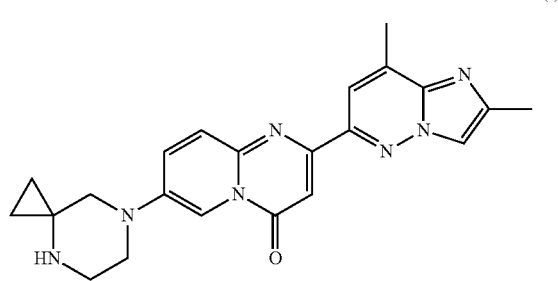

which comprises:

a) reacting a compound of formula (IV)

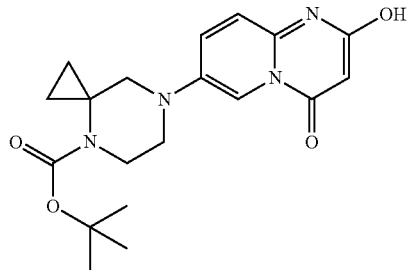

(IV)

with tosyl chloride when X is pTol-SO₃—, methanesulfonyl chloride when X is CH₃SO₃—, triflyl chloride when X is CF₃SO₃— or phenylsulfonylchloride when X is phenyl-SO₃—, and in the presence of a base, in particular wherein the base is an organic base or basic alkali metal salts, more particularly wherein the base is nitrogen-containing heterocycle, tertiary amine or basic alkali metal salts, most particularly wherein the base is a tertiary amine;

with POCl₃ when X is Cl;

with POBr₃ when X is Br; or with, Ph₃PI₂ or POCl₃ followed by NaI or CuI, when X is I.

as previously described, to obtain a compound of formula (III):

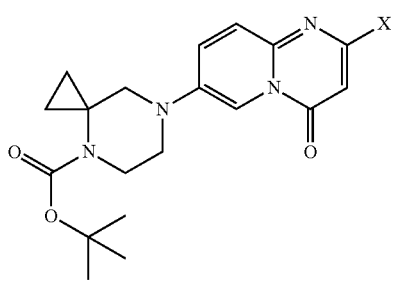

(III)

wherein X is an alkyl or aryl sulfonate (such as pTolSO₃—, CH₃SO₃—, phenyl-SO₃—), fluorinated alkyl or aryl sulfonates (such as CF₃SO₃—, nonaflate), or a halide (such as Cl, Br, or I), b) reacting said compound of formula (III), (III$_a$') or (III$_b$'), in particular with a compound of formula (III'), more particularly with a compound of formula (III')

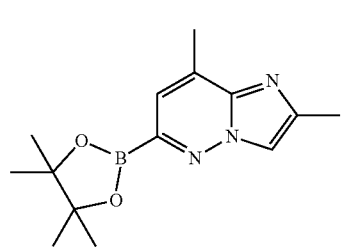

(III')

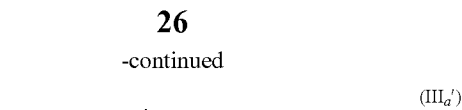

(III$_a$')

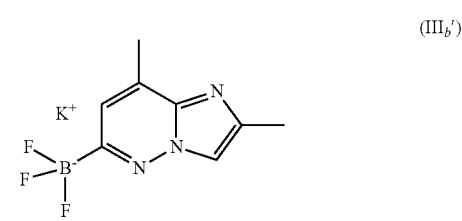

(III$_b$')

in the presence of a palladium catalyst or nickel catalyst, in particular in presence of a palladium catalyst, optionally in presence of a base, to obtain a compound of formula (II):

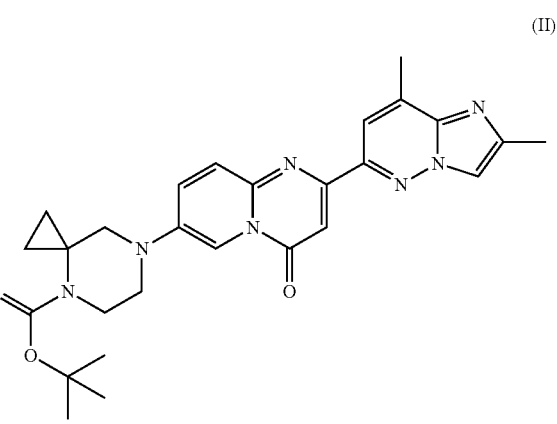

(II)

as previously described;

c) reacting said compound of formula (II) with a strong acid as previously described.

In a particular embodiment of aspect 10, the present invention provides a process for the preparation of a compound of formula (I) or the HCl salt thereof:

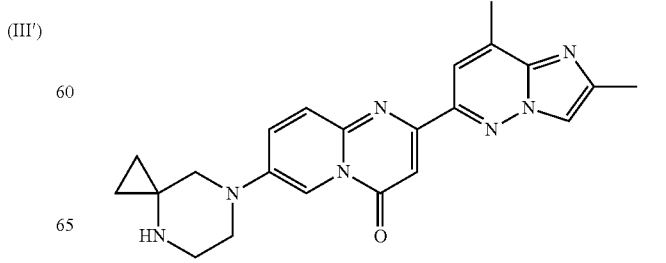

(I)

which comprises:

a) reacting a compound of formula (IV)

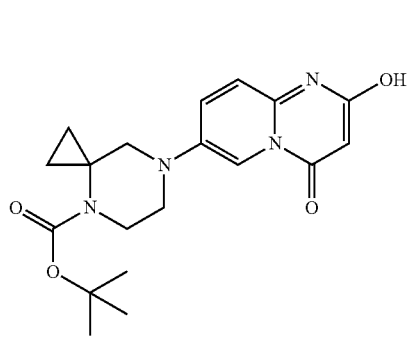
(IV)

when X is pTol-SO$_3$—, CH$_3$SO$_3$—, CF$_3$SO$_3$— or phenyl-SO$_3$— with tosyl chloride, methanesulfonyl chloride, triflyl chloride or phenylsulfonylchloride respectively and in the presence of a base, in particular wherein the base is an organic base or basic alkali metal salts, more particularly wherein the base is nitrogen-containing heterocycle, tertiary amine or basic alkali metal salts, most particularly wherein the base is a tertiary amine;

as previously described, to obtain a compound of formula (III):

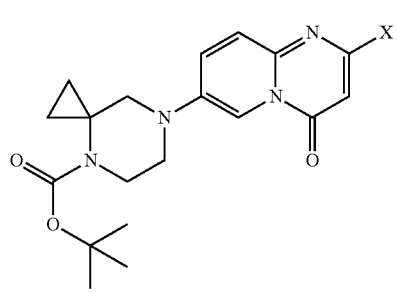
(III)

wherein X is an alkyl or aryl sulfonate (such as pTolSO$_3$—, CH$_3$SO$_3$—, phenyl-SO$_3$—), fluorinated alkyl or aryl sulfonates (such as CF$_3$SO$_3$—, nonaflate), b) reacting said compound of formula (III) with a compound of formula (III')

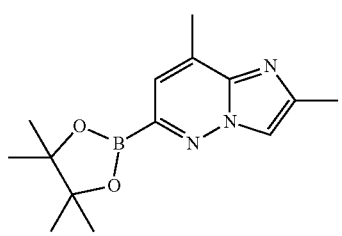
(III')

in the presence of a palladium catalyst or nickel catalyst, in particular in presence of a palladium catalyst, optionally in presence of a base, to obtain a compound of formula (II):

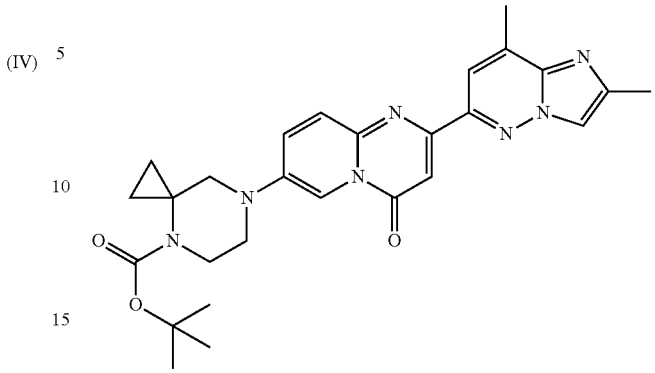
(II)

as previously described;

c) reacting said compound of formula (II) with a strong acid as previously described.

In a more particular embodiment of aspect 10, the present invention provides a process for the preparation of a compound of formula (I) or the HCl salt thereof:

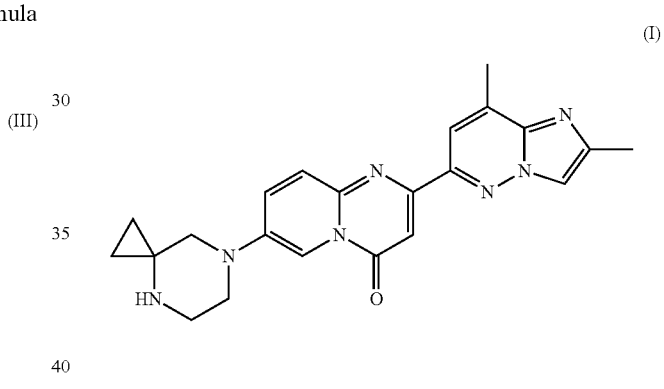
(I)

which comprises:

a) reacting a compound of formula (IV)

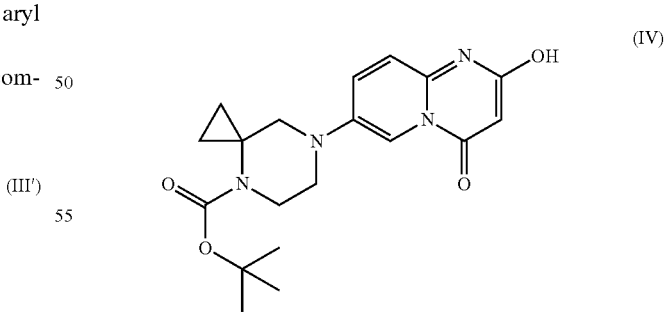
(IV)

with tosyl chloride and in the presence of a base, in particular wherein the base is an organic base or basic alkali metal salts, more particularly wherein the base is nitrogen-containing heterocycle, tertiary amine or basic alkali metal salts, most particularly wherein the base is a tertiary amine, as previously described, to obtain a compound of formula (III$_a$)

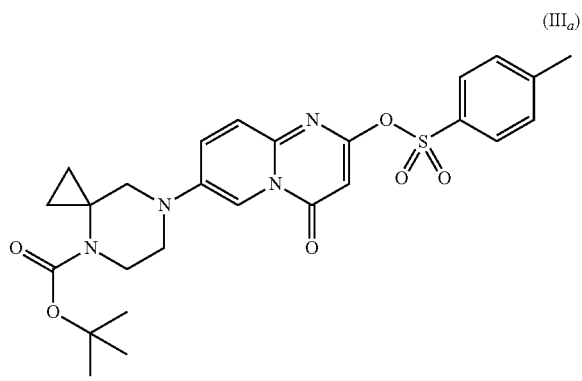 [SMILES: Cc1ccc(S(=O)(=O)Oc2cc(=O)n3cc(N4CCN(C(=O)OC(C)(C)C)C5(CC5)C4)ccc3n2)cc1]
(IIIa)

b) reacting said compound of formula (IIIa) with a compound of formula (III')

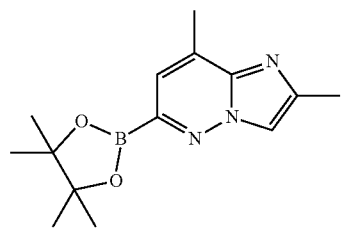
(III')

in the presence of a palladium catalyst or nickel catalyst, in particular in presence of a palladium catalyst, optionally in presence of a base, to obtain a compound of formula (II):

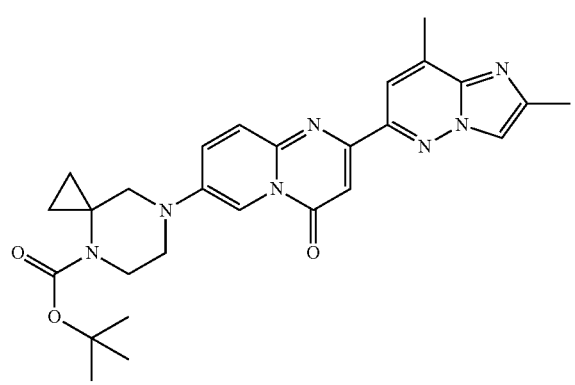
(II)

as previously described;

c) reacting said compound of formula (II) with a strong acid as previously described.

In another embodiment (aspect 11), the present invention provides a process for the preparation of a compound of formula (I) or the HCl salt thereof:

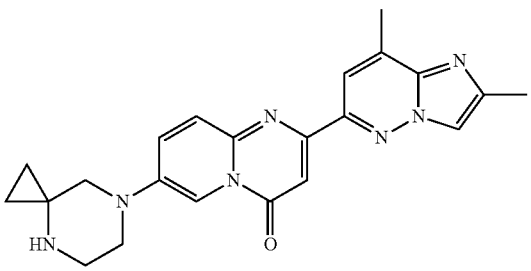
(I)

which comprises:

a) reacting a compound of formula (V)

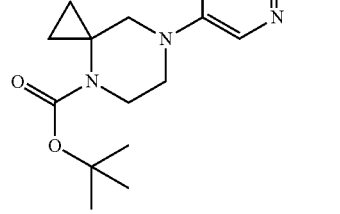
(V)

with di-tert-butyl malonate to obtain a compound of formula (IV)

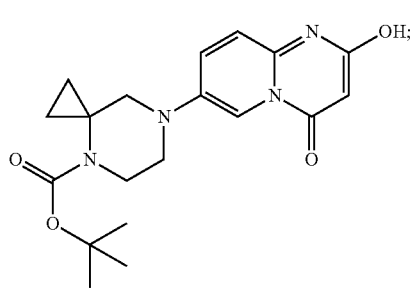
(IV)

b) reacting said compound of formula (IV)

with tosyl chloride when X is pTol-$SO_3$—, methanesulfonyl chloride when X is $CH_3SO_3$—, triflyl chloride when X is $CF_3SO_3$— or phenylsulfonylchloride when X is phenyl-$SO_3$—, and in the presence of a base, in particular wherein the base is an organic base or basic alkali metal salts, more particularly wherein the base is nitrogen-containing heterocycle, tertiary amine or basic alkali metal salts, most particularly wherein the base is a tertiary amine;

with $POCl_3$ when X is Cl;

with $POBr_3$ when X is Br; or with, $Ph_3PI_2$ or $POCl_3$ followed by NaI or CuI, when X is I.

as previously described, to obtain a compound of formula (III)

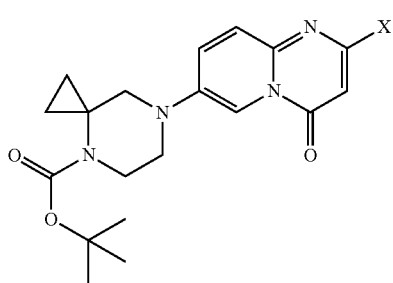

(III)

wherein X is an alkyl or aryl sulfonate (such as pTolSO$_3$—, CH$_3$SO$_3$—, phenyl-SO$_3$—), fluorinated alkyl or aryl sulfonates (such as CF$_3$SO$_3$—, nonaflate), or a halide (such as Cl, Br, or I);

c) reacting said compound of formula (III) with a compound of formula (III'), (III$_a$') or (III$_b$'), in particular with a compound of formula (III'), more particularly with a compound of formula (III')

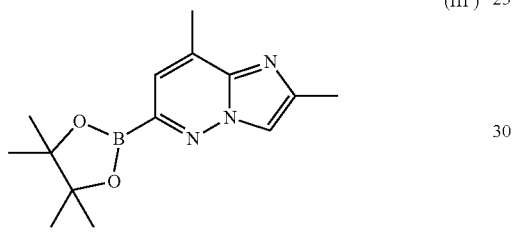

(III')

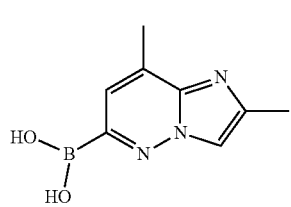

(III$_a$')

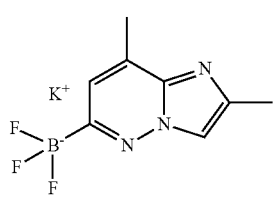

(III$_b$')

in the presence of a palladium catalyst or nickel catalyst, in particular in presence of a palladium catalyst, optionally in presence of a base, to obtain a compound of formula (II):

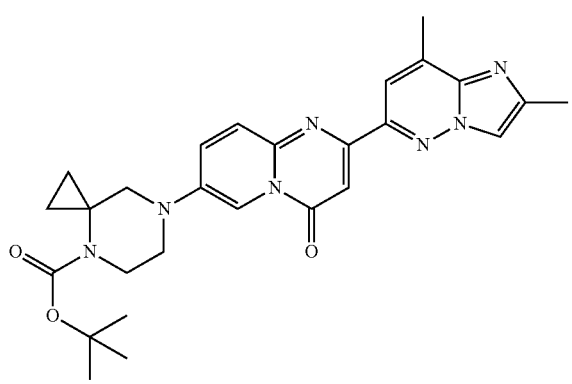

(II)

as previously described;

d) reacting said compound of formula (II) with a strong acid as previously described.

In a particular embodiment of aspect 11, the present invention provides a process for the preparation of a compound of formula (I) or the HCl salt thereof:

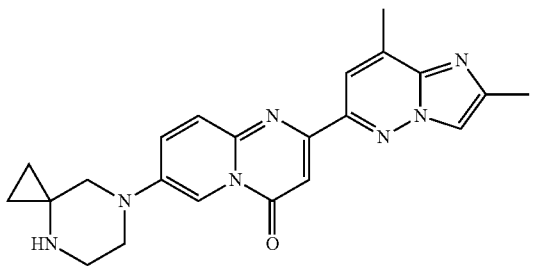

(I)

which comprises:

a) reacting a compound of formula (V)

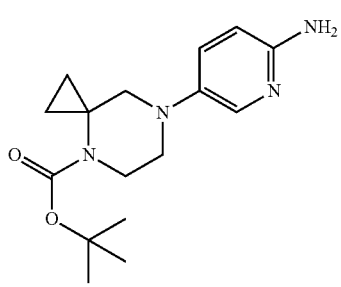

(V)

with di-tert-butyl malonate to obtain a compound of formula (IV)

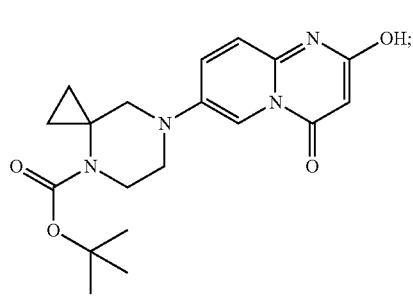
(IV)

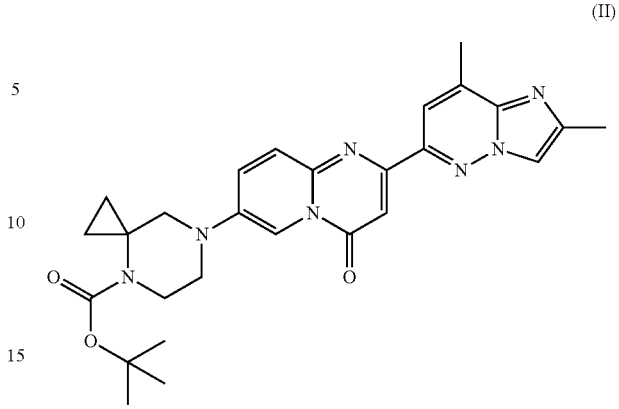
(II)

b) reacting said compound of formula (IV) when X is pTol-SO$_3$—, CH$_3$SO$_3$—, CF$_3$SO$_3$— or phenyl-SO$_3$—, with tosyl chloride, methanesulfonyl chloride, triflyl chloride or phenylsulfonylchloride respectively and in the presence of a base, in particular wherein the base is an organic base or basic alkali metal salts, more particularly wherein the base is nitrogen-containing heterocycle, tertiary amine or basic alkali metal salts, most particularly wherein the base is a tertiary amine as previously described, to obtain a compound of formula (III)

as previously described;

d) reacting said compound of formula (II) with a strong acid as previously described.

In a more particular embodiment of aspect 11, the present invention provides a process for the preparation of a compound of formula (I) or the HCl salt thereof:

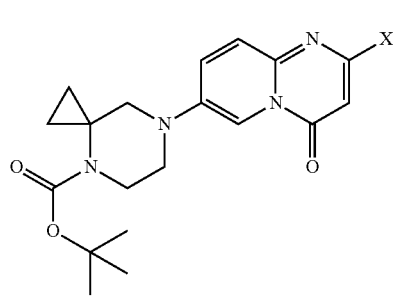
(III)

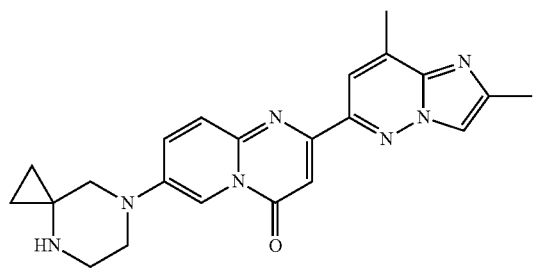
(I)

wherein X is an alkyl or aryl sulfonate (such as pTolSO$_3$—, CH$_3$SO$_3$—, phenyl-SO$_3$—), fluorinated alkyl or aryl sulfonates (such as CF$_3$SO$_3$—, nonaflate);

c) reacting said compound of formula (III) with a compound of formula (III')

which comprises:

a) reacting a compound of formula (V)

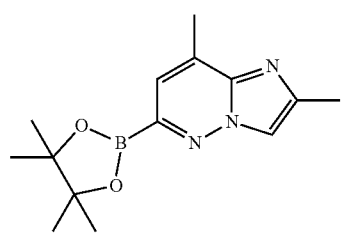
(III')

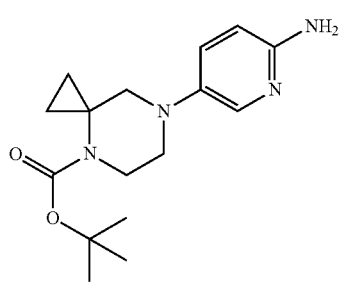
(V)

in the presence of a palladium catalyst or nickel catalyst, in particular in presence of a palladium catalyst, optionally in presence of a base, to obtain a compound of formula (II):

with di-tert-butyl malonate to obtain a compound of formula (IV)

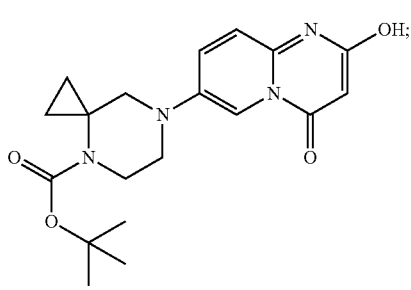

(IV)

b) reacting said compound of formula (IV) with tosyl chloride and in the presence of a tertiary amine, as previously described, to obtain a compound of formula (III$_a$)

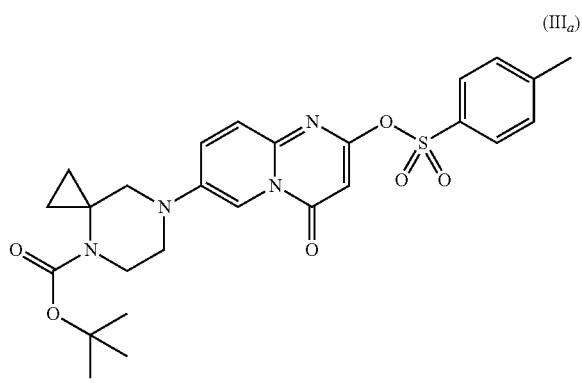 [SMILES: Cc1ccc(S(=O)(=O)Oc2cc(=O)n3cc(N4CCN(C(=O)OC(C)(C)C)C5(CC5)C4)ccc3n2)cc1]

(III$_a$)

c) reacting said compound of formula (III$_a$) with a compound of formula (III')

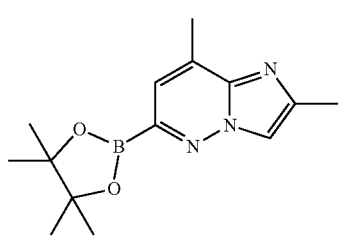

(III')

in the presence of a palladium catalyst or nickel catalyst, in particular in presence of a palladium catalyst, optionally in presence of a base, to obtain a compound of formula (II):

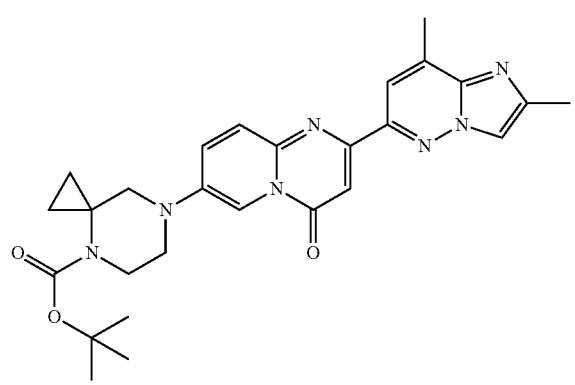

(II)

as previously described;
d) reacting said compound of formula (II) with a strong acid as previously described.

In another embodiment (aspect 12), the present invention provides a process for the preparation of a compound of formula (III") in accordance with scheme 3:

Scheme 3

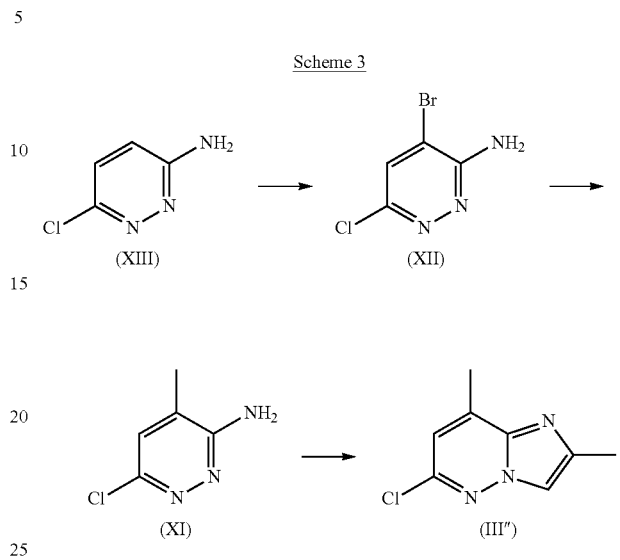

In particular according to the invention, a compound of formula (XII) is prepared by reacting a compound of formula (XIII) with 1,3-dibromo-5,5-dimethylhydantoin (DBDMH), N-bromo-succinimide or bromine, optionally with sodium acetate or sodium bicarbonate and in the presence of a solvent such as alcohols (e.g. methanol or ethanol). Furthermore a compound of (XI) is prepared by reacting a compound of formula (XII) with methyl magnesium chloride or bromide, methylboronic acid, methyl borate, dimethylzinc or methyllithium, optionally in the presence of zinc chloride or with dimethylzinc in methyltetrahydrofuran or THF, in the presence of a catalyst (such as Pd(PPh$_3$)$_4$, PdCl$_2$, Pd(OAc)$_2$, Pd$_2$(dba)$_3$, Pd(PPh$_3$)$_2$Cl$_{12}$, PdCl$_2$(dppf), PdCl$_2$(dppf).CH$_2$Cl$_2$, PdCl$_2$(dppp), Cyclopentadienyl allyl palladium, allylpalladium(II) chloride dimer (Pd(allyl)Cl)$_2$ (2-Butenyl)chloropalladium dimer, (2-Methylallyl) palladium(II) chloride dimer, palladium(1-phenylallyl)chloride dimer, di-μ-chlorobis[2'-(amino-N)[1,1'-biphenyl]-2-yl-C]dipalladium(II), Di-μ-chlorobis[2-[(dimethylamino)methyl]phenyl-C,N]dipalladium(II), dichloro[9,9-dimethyl-4,5-bis(diphenylphosphino)xanthene]palladium (Pd(XantPhos)Cl$_2$), in particular in the presence Pd(PPh$_3$)$_4$). A compound of formula (III") is prepared by reacting chloroacteone with a compound of formula (XI) in the presence of tertiary amine and sodium bromide.

Alternatively compound of formula (III") can be prepared in accordance with the process described in WO2015173181.

The present application further discloses a process for the preparation of compound of formula (III$_a$') or (III$_b$') in accordance with scheme 4.

Scheme 4

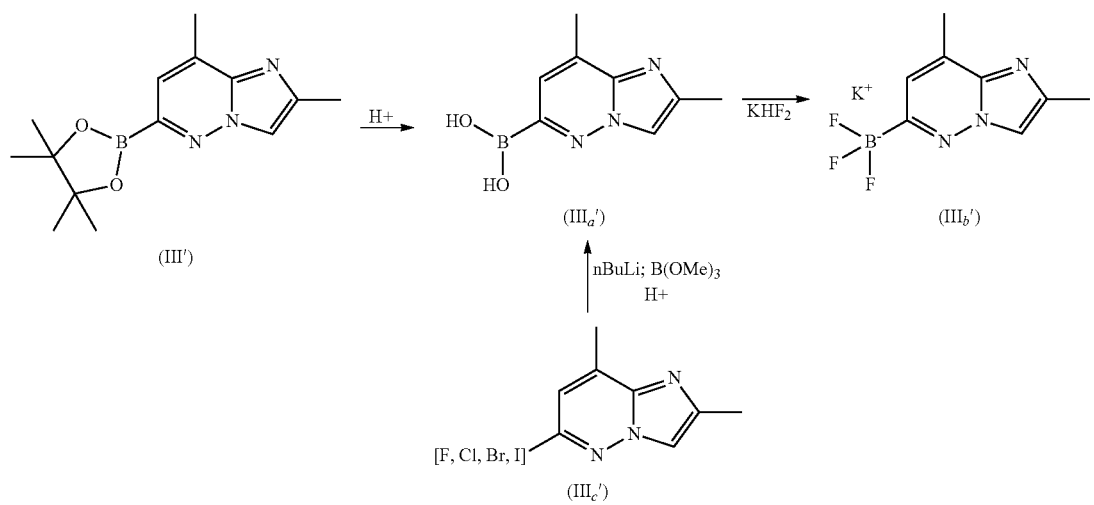

A particular embodiment of the invention also relates to a pharmaceutical composition comprising the compound of formula (I) obtained according to as described herein and at least one pharmaceutically acceptable excipient.

A further particular embodiment of the invention also relates to a compound of formula (I) obtained by the process as described herein for use as therapeutically active substances.

The starting materials and reagents, which do not have their synthetic route explicitly disclosed herein, are generally available from commercial sources or are readily prepared using methods well known to the person skilled in the art.

In general, the nomenclature used in this Application is based on AUTONOM™ 2000, a Beilstein Institute computerized system for the generation of IUPAC systematic nomenclature. Chemical structures shown herein were prepared using MDL ISIS™ version 2.5 SP2. Any open valency appearing on a carbon, oxygen or nitrogen atom in the structures herein indicates the presence of a hydrogen atom.

The following examples are provided for the purpose of further illustration and are not intended to limit the scope of the claimed invention.

In the present application, the following abbreviations and definitions are used: br (broad); BuLi (butyllithium); CDCl$_3$ (deuterated chloroform); d (doublet); eq. (equivalent); g (gram); GC (gas chromatography); h (hour); HCl (hydrochloric acid); H$_2$O (water); HPLC (High-Performance Liquid Chromatography); ISP (Isotopic Spin Population); KOH (Potassium Hydroxide); L (liter); LDA (Lithium Diisopropylamide); LCMS (Liquid chromatography-mass spectrometry); M (Molar); m (multiplet); MS (Mass Spectroscopy); mL (milliliter); NaOH (sodium hydroxide); NMR (nuclear magnetic resonance); Pd(dba)$_3$ (tris(dibenzylideneacetone) dipalladium(0)); Pd(Xantphos)Cl$_2$ (Dichloro[9,9-dimethyl-4,5-bis(diphenylphosphino)-xanthene]palladium(II)); s (singlet); sec (second); t (triplet); t-Bu Brett Phos (2-(Di-tert-butylphosphino)-2',4',6'-triisopropyl-3,6-dimethoxy-1,1'-biphenyl); THF (tetrahydrofuran);

EXAMPLE 1 tert-Butyl 7-(6-chloro-3-pyridyl)-4,7-diazaspiro[2.5]octane-4-carboxylate

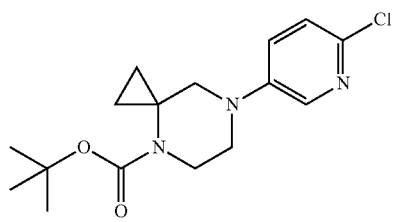 [SMILES: CC(C)(C)OC(=O)N1CCN(c2ccc(Cl)nc2)CC12CC2]

5-Bromo-2-chloropyridine (85.0 g, 442 mmol), tert-butyl 4,7-diazaspiro[2.5]octane-4-carboxylate (102 g, 442 mmol) and Me-THF (722 g) were charged into a reaction vessel. After 10 minutes stirring, most of the solids were dissolved and [Pd(Xantphos)Cl$_2$] (3.34 g) was added followed after 5 minutes by a solution of sodium tert-butanolate (56.3 g, 574 mmol) in Me-THF (173 g). The reaction mixture was stirred at 70° C. for 1.25 hours, cooled to room temperature and water (595 g) and 1-propylacetate (378 g) were added. After vigorous stirring, the phases were separated, the organic phase was washed with a second portion of water (425 g) and with a mixture of water (425 g) and brine (25 mL). The organic phase was treated with active charcoal (6.8 g), filtered and concentrated under reduced pressure to afford a brown oil, which was dissolved in tert-amyl-methyl-ether (347 g) at reflux. The solution was cooled slowly to room temperature. After stirring 18 hours at room temperature, n-heptane (205 g) was added and the suspension was further cooled to −10° C. The precipitate was filtered off and dried under high vacuum to afford tert-butyl 7-(6-chloro-3-pyridyl)-4,7-diazaspiro[2.5]octane-4-carboxylate (110.9 g, 77.5%) as a beige solid.

$^1$H-NMR (CDCl$_3$, 600 MHz): 7.95 (d, 1H); 7.18-7.14 (m, 1H); 7.13-7.09 (m, 1H); 3.79-3.63 (m, 2H); 3.24-3.12 (m, 2H); 2.96 (s, 2H); 1.47 (s, 9H); 1.11-1.04 (m, 2H); 0.90-0.79 (m, 2H); LCMS: 324.15, 326.15 (M+H$^+$)

EXAMPLE 2 tert-butyl 7-(6-amino-3-pyridyl)-4,7-diazaspiro[2.5]octane-4-carboxylate

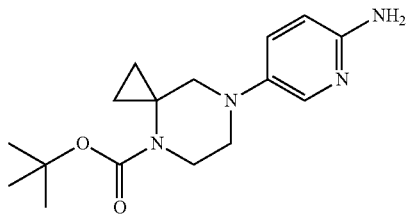 [SMILES: CC(C)(C)OC(=O)N1CCN(c2ccc(N)nc2)CC12CC2]

An autoclave equipped with an ascending pipe was filled with ammonia (78.7 g, 15 eq; 10 eq are sufficient) at −70° C. Another autoclave was charged with tert-butyl 7-(6-chloro-3-pyridyl)-4,7-diazaspiro[2.5]octane-4-carboxylate (100 g, 309 mmol), sodium tert-butanolate (32.6 g, 340 mmol) and dioxane (800 mL). After 10 minutes stirring at room temperature under Ar, a solution of $Pd_2(dba)_3$ (1.41 g, 1.54 mmol) and tBuBrettPhos (1.50 g, 3.09 mmol) in dioxane (180 mL) was added. Thereafter, the connected ammonia vessel was warmed with a warm water bath and the connecting valve was opened. The autoclave was warmed to 30° C. and the reaction mixture stirred 5 hours at this temperature. The ammonia vessel was closed and disconnected. The excess ammonia was washed out of the autoclave with Argon. The reaction solution was poured into a separating funnel, the autoclave washed with ethyl acetate (300 mL) and water (100 mL) and these two solvent portions were added to the separating funnel. The biphasic mixture was further diluted with ethyl acetate (900 mL) and water (1000 mL). After vigorous stirring, the phases were separated. The organic phase was washed with a mixture of water (500 mL) and brine (10 mL). The combined aqueous phases were extracted twice with ethyl acetate (500 mL). The combined organic phases were treated with active charcoal (3.70 g, 309 mmol), filtered and the filtrate was concentrated under reduced pressure to afford a thick brown oil. This oil was dissolved in 1-propyl acetate (160 mL) at 45-50° C. and n-heptane (940 mL) was added drop wise within 1.5 hours. The suspension was cooled slowly to −5° C., stirred 4 hours at −5° C. and filtered. The precipitate was washed with cold n-heptane and dried under high vacuum at 50° C. to afford tert-butyl 7-(6-amino-3-pyridyl)-4,7-diazaspiro[2.5]octane-4-carboxylate (81.4 g, 86.5%) as a beige solid.
$^1$H-NMR (CDCl$_3$, 600 MHz): 7.71 (d, 1H); 7.12 (dd, 1H); 6.47 (d, 1H); 4.18 (br s, 2H); 3.74-3.58 (m, 2H); 3.09-2.94 (m, 2H); 2.81 (s, 2H); 1.52-1.39 (m, 9H); 1.17-0.98 (m, 2H); 0.92-0.75 (m, 2H); LCMS: 305.20 (M+H$^+$)

EXAMPLE 3 tert-butyl 7-(6-amino-3-pyridyl)-4,7-diazaspiro[2.5]octane-4-carboxylate

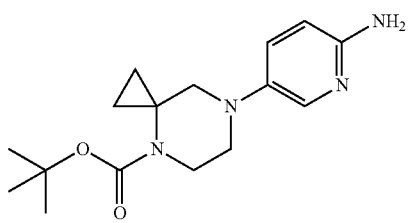 [SMILES: CC(C)(C)OC(=O)N1CCN(c2ccc(N)nc2)CC12CC2]

An autoclave was charged with tert-butyl 7-(6-chloro-3-pyridyl)-4,7-diazaspiro[2.5]octane-4-carboxylate (339 mg, 1 mmol), sodium tert-butanolate (109 mg, 1.1 mmol) and dioxane (5 mL). After 5 minutes stirring at room temperature under Argon [Pd(allyl)(tBuBrettPhos)]OTf (4 mg, 5 µmol) was added. Thereafter, the autoclave was closed and connected to an ammonia tank, the valve was open and ammonia (230 mg, 13.5 mmol) was introduced into the autoclave. The valve was closed and the autoclave disconnected. The autoclave was warmed to 30° C. and the reaction mixture stirred 4 hours at this temperature. Then the autoclave was opened and the excess ammonia was washed out of the autoclave with Argon. The reaction solution was poured into a flask and taken to dryness under reduced pressure. The residue was purified by chromatography over silica gel (eluent: dichloromethane/ethyl acetate to dichloromethane/methanol). After evaporation of the solvents tert-butyl 7-(6-amino-3-pyridyl)-4,7-diazaspiro[2.5]octane-4-carboxylate (283 mg, 93%) was isolated as a brown oil containing 4% dichloromethane and 3% ethyl acetate.

EXAMPLE 4 tert-butyl 7-(6-nitro-3-pyridyl)-4,7-diazaspiro[2.5]octane-4-carboxylate

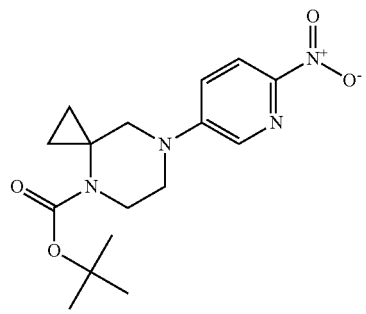 [SMILES: CC(C)(C)OC(=O)N1CCN(c2ccc([N+](=O)[O-])nc2)CC12CC2]

tert-Butyl 4,7-diazaspiro[2.5]octane-4-carboxylate oxalate salt (2.46 kg, 8.13 mol), 5-bromo-2-nitro-pyridine (1.50 kg, 7.39 mol) and dimethyl sulfoxide (7.80 L) were charged into a reaction vessel pre-heated to 35° C. With stirring, and keeping the temperature below 40° C., lithium chloride (1.25 kg, 25.6 mol) was added portion-wise followed by tetramethylguanidine (2.98 kg, 25.9 mol). Dimethyl sulfoxide (450 mL) was used to rinse the feed line. The reaction mixture was stirred at 79° C. for 8 hours, cooled to 70° C. and water (2.48 L) was added within 2 hours. After stirring at 70° C. for an additional 1 hour, the precipitate was filtered off and washed with water (4.5 L) three times. The precipitate was dissolved in ethyl acetate (15 L) and water (7.5 L) at reflux temperature. The phases were separated at 60° C. and n-heptane (7.5 L) was added to the organic layer at 60° C. within 30 minutes. The solution was cooled to 0° C. in 2 hours and further stirred at 0° C. for 1 hour. The precipitate was filtered off, washed with a mixture of ethyl acetate (750 mL)/n-heptane (375 mL) twice and dried under reduced pressure to afford 1.89 kg (76.4%) of tert-butyl 7-(6-nitro-3-pyridyl)-4,7-diazaspiro[2.5]octane-4-carboxylate as a yellow to light brown solid.
$^1$H-NMR (CDCl$_3$, 600 MHz): 8.16 (d, 1H); 8.07 (d, 1H); 7.15 (dd, 1H); 3.80-3.72 (m, 2H); 3.49-3.41 (m, 2H); 3.23 (s, 2H); 1.48 (s, 9H); 1.16-1.08 (m, 2H); 0.92-0.85 (m, 2H); LCMS: 335.17 (M+H$^+$)

EXAMPLE 5 tert-butyl 7-(2-hydroxy-4-oxo-pyrido[1,2-a]pyrimidin-7-yl)-4,7-diazaspiro[2.5]octane-4-carboxylate

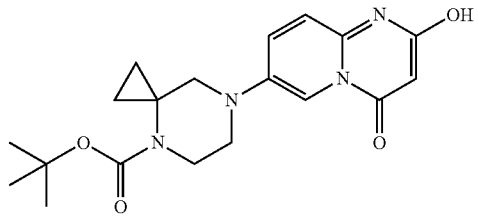 [SMILES: CC(C)(C)OC(=O)N1CCN(c2ccc3nc(O)cc(=O)n3c2)CC12CC2]

tert-Butyl 7-(6-amino-3-pyridyl)-4,7-diazaspiro[2.5]octane-4-carboxylate (80.0 g, 263 mmol) was dissolved in anisole (800 mL) and di-tert-butyl malonate (71.1 g, 315 mmol) was added. The solution was stirred 3.5 hours at 145° C. then cooled to room temperature. The precipitate was filtered off, washed with toluene (in portions, 320 mL in total) and dried under high vacuum at 50° C. to afford tert-butyl 7-(2-hydroxy-4-oxo-pyrido[1,2-a]pyrimidin-7-yl)-4,7-diazaspiro[2.5]octane-4-carboxylate (65.6 g, 67%) as a light pink powder.

$^1$H-NMR (CDCl$_3$, 600 MHz): 8.46 (d, 1H); 7.74 (dd, 1H); 7.52 (d, 1H); 5.37 (s, 2H); 3.83-3.69 (m, 2H); 3.23 (t, 2H); 3.01 (s, 2H); 1.48 (s, 9H); 1.17-1.03 (m, 2H); 0.95-0.75 (m, 2H); LCMS: 373.19 (M+H$^+$)

EXAMPLE 6 tert-butyl 7-(2-hydroxy-4-oxo-pyrido[1,2-a]pyrimidin-7-yl)-4,7-diazaspiro[2.5]octane-4-carboxylate

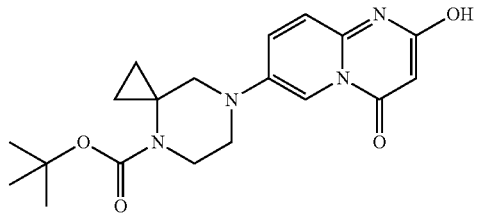 [SMILES: CC(C)(C)OC(=O)N1CCN(c2ccc3nc(O)cc(=O)n3c2)CC12CC2]

tert-Butyl 7-(6-nitro-3-pyridyl)-4,7-diazaspiro[2.5]octane-4-carboxylate (950 g, 2.84 mol), Pt 1%, V 2% on active charcoal (95.1 g, 2 mmol) and ethyl acetate (9.5 L) were charged into an autoclave that was pressurized with hydrogen gas to 3 bar. The reaction mixture was stirred at room temperature for 6 hours. The excess hydrogen was vented. The reaction mixture was filtered, the catalyst was washed with ethyl acetate (0.95 L) three times. The filtrate was concentrated under reduced pressure and the solvent exchanged to anisole (add two portions of 2.85 L and 5.18 L) by distillation. Di tert-butyl malonate (921.7 g, 4.26 mol) was added and the charging line was rinsed with anisole (618 mL) and the reaction mixture was stirred at 125-135° C. for 8 hours. It may be necessary to distill off the by-product tert-butanol to reach this temperature. The progress of the reaction was followed eg. by HPLC. If the reaction stalls, the temperature is increased to 135-145° C. and checked for progress after 1 hour. When the reaction was complete, the batch was cooled to room temperature and stirred at room temperature for 4 hours. The precipitate was filtered off, washed with toluene (3.55 L) and dried under vacuum at 60° C. to afford tert-butyl 7-(2-hydroxy-4-oxo-pyrido[1,2-a]pyrimidin-7-yl)-4,7-diazaspiro[2.5]octane-4-carboxylate (861.0 g, 81.4%) as a yellow to light brown solid.

EXAMPLE 7 tert-butyl 7-[4-oxo-2-(p-tolylsulfonyloxy)pyrido[1,2-a]pyrimidin-7-yl]-4,7-diazaspiro[2.5]octane-4-carboxylate

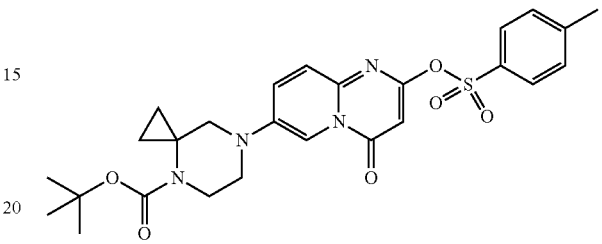

A reactor was charged with tert-butyl 7-(2-hydroxy-4-oxo-pyrido[1,2-a]pyrimidin-7-yl)-4,7-diazaspiro[2.5]octane-4-carboxylate (920 g, 2.47 mol) and then triethylamine (325 g, 3.21 mol), followed by tosyl chloride (527.1 g, 2.77 mol) and dichloromethane (4.6 L). The reaction mixture was stirred at 20-25° C. for at least three hours. Upon complete reaction, the organic solution was washed with a prepared solution of HCl (32%, 247.8 mL) and water (4.6 L), followed by a prepared solution of sodium hydroxide (432.3 mL of a 30% stock solution) and water (3.9 L) in that order. The organic phase was finally washed with water (4.8 L) and then dichloromethane was nearly completely distilled off under reduced pressure at 50-55° C. Ethyl acetate (920 mL) was added and distilled twice at this temperature under reduced pressure, and then ethyl acetate (4.8 L) was added and the suspension cooled to 20-25° C. over two hours. n-Heptane (944.4 mL) was added and the mixture was cooled to 0-5° C. and then stirred for an additional 3 hours. The precipitate was filtered off, washed with a prepared solution of ethyl acetate (772.8 mL) and n-heptane (147.2 mL), and then twice with n-heptane (2.6 L). The solid was dried under vacuum at 45-50° C. to afford 1122.6 g (86.3%) tert-butyl 7-[4-oxo-2-(p-tolylsulfonyloxy)pyrido[1,2-a]pyrimidin-7-yl]-4,7-diazaspiro[2.5]octane-4-carboxylate as yellow crystals.

$^1$H-NMR (CDCl$_3$, 600 MHz): 8.32 (d, 1H); 8.00-7.89 (m, 2H); 7.66 (dd, 1H); 7.50 (d, 1H); 7.36 (d, 2H); 6.04 (s, 1H); 3.80-3.68 (m, 2H); 3.23 (t, 2H); 3.01 (s, 2H); 1.48 (s, 9H); 1.15-1.04 (m, 2H); 0.92-0.82 (m, 2H); LCMS: 527.20 (M+H$^+$)

EXAMPLE 8

2,8-dimethyl-6-(4,4,5,5-tetramethyl-1,3,2-dioxaborolan-2-yl)imidazo[1,2-b]pyridazine

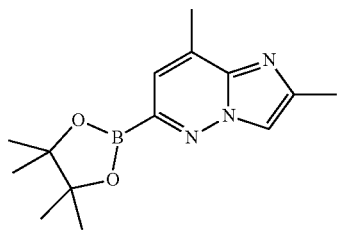

6-Chloro-2,8-dimethylimidazo[1,2-b]pyridazine (40.0 g, 220 mmol), bis pinacol diborane (69.9 g, 275 mmol) and potassium acetate (43.2 g, 440 mmol) were suspended in acetonitrile (440 mL). The suspension was heated to reflux and stirred 30 minutes at reflux, then a suspension of PdCl$_{12}$(dppf) (4.03 g, 5.51 mmol) and dppf (610 mg, 1.1 mmol) in acetonitrile (40 mL) was added. The vessel was rinsed with acetonitrile (20 mL), which were also poured into the reaction mixture. The orange suspension was further stirred at reflux, whereby acetonitrile (50 mL) were distilled off. After 4 hours, the reaction mixture was filtered off, the filter was washed with several portions of acetonitrile (in total 150 mL). The filtrate was diluted to obtain a volume of 700 mL. The 314 mmolar solution of 2,8-dimethyl-6-(4,4,5,5-tetramethyl-1,3,2-dioxaborolan-2-yl)imidazo[1,2-b]pyridazine in acetonitrile was used as such in the next step.

EXAMPLE 9

2,8-dimethyl-6-(4,4,5,5-tetramethyl-1,3,2-dioxaborolan-2-yl)imidazo[1,2-b]pyridazine

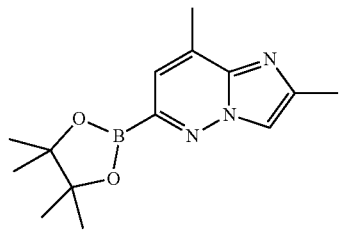

6-chloro-2,8-dimethylimidazo[1,2-b]pyridazine (29.0 g, 22.8 mmol), bis pinacol diborane (44.6, 25.1 mmol) and potassium acetate (31.3 g, 45.6 mmol) were suspended in 1-propyl acetate (365 mL). The suspension was heated to 80° C. and a solution of tricyclohexylphosphine (448 mg, 0.23 mmol) and Pd(OAc)$_2$ (179 mg, 0.11 mmol) in 1-propyl acetate (37 mL) was added within 20 minutes. After 2.5 hours further stirring at 80° C., the suspension was cooled to 40° C. and filtered at this temperature. The precipitate was washed with 1-propyl acetate (200 mL). The filtrate corresponds to 516.4 g of a 8.5% solution of 2,8-dimethyl-6-(4,4,5,5-tetramethyl-1,3,2-dioxaborolan-2-yl)imidazo[1,2-b]pyridazine in 1-propyl acetate.

EXAMPLE 10

Isolation of 2,8-dimethyl-6-(4,4,5,5-tetramethyl-1,3,2-dioxaborolan-2-yl)imidazo[1,2-b]pyridazine

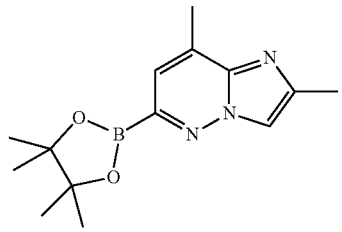

In another experiment, the above solution obtained was cooled to 0-5° C. within 3 hours. The precipitate was filtered off, washed with cold 1-propyl acetate and dried under high vacuum at 60° C. to afford 2,8-dimethyl-6-(4,4,5,5-tetramethyl-1,3,2-dioxaborolan-2-yl)imidazo[1,2-b]pyridazine (24.0 g, 55%) as a colourless solid.

$^1$H NMR (CDCl$_3$, 600 MHz,) δ ppm 7.86 (d, J=0.7 Hz, 1H), 7.20 (d, J=1.0 Hz, 1H), 2.63 (d, J=1.0 Hz, 3H), 2.51 (d, J=0.7 Hz, 3H), 1.33-1.49 (m, 12H)

EXAMPLE 11

(step 6) tert-butyl 7-[2-(2,8-dimethylimidazo[1,2-b]pyridazin-6-yl)-4-oxo-pyrido[1,2-a]pyrimidin-7-yl]-4,7-diazaspiro[2.5]octane-4-carboxylate tert-Butyl 7-[4-oxo-2-(p-tolylsulfonyloxy)pyrido[1,2-a]pyrimidin-7-yl]-4,7-diazaspiro[2.5] octane-4-carboxylate (25 g, 47.5 mmol), 2,8-dimethyl-6-(4,4,5,5-tetramethyl-1,3,2-dioxaborolan-2-yl)imidazo[1,2-b]pyridazine (314 mM in acetonitrile, 191 mL, 59.8 mmol), PdCl$_2$(dppf) (868 mg, 1.19 mmol) and aqueous potassium carbonate 4.07 M (17.1 mL, 69.8 mmol) were charged into a reaction vessel. The reaction mixture was stirred at reflux for 3 hours, cooled overnight to room temperature and filtered. The precipitate was washed with several portions of acetonitrile (146 mL in total), then suspended in methyl-THF (750 mL) and methanol (75 mL). Aqueous sodium hydrogen carbonate 5% (250 mL) was added, the mixture was vigorously stirred at 35° C. The phases were separated, the organic phase was washed again with aqueous sodium hydrogen carbonate 5% (250 mL). The organic phase was treated with active charcoal for 1 hour at room temperature, filtered and the filtrate was concentrated under reduced pressure at 60° C. to a volume of 225 mL, heated to reflux then cooled to room temperature, stirred at room temperature for 16 hours, then cooled to 0° C. and stirred at 0° C. for 3 hours. The precipitate was filtered off, washed with n-heptane (60 mL) and dried under high vacuum at 55° C. to afford tert-butyl 7-[2-(2,8-dimethylimidazo[1,2-b]pyridazin-6-yl)-4-oxo-pyrido[1,2-a]pyrimidin-7-yl]-4,7-diazaspiro[2.5]octane-4-carboxylate (20.13 g, 84.5%) as a yellow solid.

This solid could be recrystallized in the following manner: 15 g of the above solid was dissolved at reflux in toluene (135 mL) and ethanol (15 mL). The solution was slowly cooled to room temperature, stirred 16 hours at room temperature, then cooled to 0° C. and stirred at 0° C. for 4 hours. The precipitate was filtered off, washed with cold toluene and dried under high vacuum at 55° C. to afford tert-butyl 7-[2-(2,8-dimethylimidazo[1,2-b]pyridazin-6-yl)-4-oxo-pyrido[1,2-a]pyrimidin-7-yl]-4,7-diazaspiro[2.5]octane-4-carboxylate (11.92 g, 79.5%) as a yellow-green solid.

$^1$H-NMR (CDCl$_3$, 600 MHz): 8.44 (d, 1H); 7.93 (d, 1H); 7.96-7.89 (m, 1H); 7.80 (d, 1H); 7.76-7.72 (m, 1H); 7.70-7.63 (m, 1H); 7.38 (s, 1H); 3.85-3.69 (m, 2H); 3.28 (t, 2H);

3.07 (s, 2H); 2.74 (d, 3H); 2.55 (s, 3H); 1.49 (s, 9H); 1.16-1.09 (m, 2H); 0.93-0.86 (m, 2H); LCMS: 502.26 (M+H⁺)

EXAMPLE 12 tert-butyl 7-[2-(2,8-dimethylimidazo[1,2-b]pyridazin-6-yl)-4-oxo-pyrido[1,2-a]pyrimidin-7-yl]-4,7-diazaspiro[2.5]octane-4-carboxylate

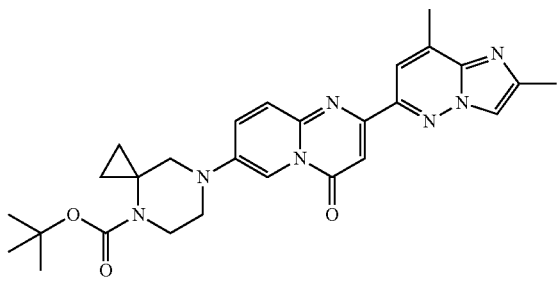 [SMILES: Cc1cn2nc(-c3cc(=O)n4cc(N5CCN(C(=O)OC(C)(C)C)C6(CC6)C5)ccc4n3)cc(C)c2n1]

6-chloro-2,8-dimethylimidazo[1,2-b]pyridazine (4.14 g, 22.8 mmol), bis pinacol diborane (6.37 g, 25.1 mmol) and potassium acetate (4.47 g, 45.6 mmol) were suspended in 1-propyl acetate (59 mL). The suspension was heated to 80° C. and a solution of tricyclohexylphosphine (63.9 mg, 0.23 mmol) and Pd(OAc)₂ (25.6 mg, 0.11 mmol) in 1-propyl acetate (6 mL) was added within 20 minutes. After 2.5 hours further stirring at 80° C., the suspension was cooled to 40° C. and filtered at this temperature. The precipitate was washed with 1-propyl acetate (32 mL). The filtrate corresponds to 74.6 g of a 8.5% solution of 2,8-dimethyl-6-(4,4,5,5-tetramethyl-1,3,2-dioxaborolan-2-yl)imidazo[1,2-b]pyridazine in 1-propyl acetate.

A reaction vessel was charged with tert-butyl 7-[4-oxo-2-(p-tolylsulfonyloxy)pyrido[1,2-a]pyrimidin-7-yl]-4,7-diazaspiro[2.5]octane-4-carboxylate (10.0 g, 19.0 mmol), tricyclohexylphosphine (58.6 mg, 0.21 mmol) and Pd(OAc)₂ (21.3 mg, 0.10 mmol) and 1-propyl acetate (42 mL) and a solution of potassium carbonate (5.25 g, 38.0 mmol) in water (19.0 mL) was added. The suspension was heated to 70° C. and the solution of 2,8-dimethyl-6-(4,4,5,5-tetramethyl-1,3,2-dioxaborolan-2-yl)imidazo[1,2-b]pyridazine in 1-propyl acetate was added within 30 minutes. The mixture was stirred for 2 hours at 70-75° C. The suspension was cooled to 40° C., water (10 mL) was added. The suspension was aged for 30 minutes. The crude product was filtered off and rinsed with 1-propyl acetate (41 mL). The crude product was taken up in toluene (100 mL), 5% aqueous NaHCO₃-solution (30 mL) and 1-propanol (20.0 mL). The mixture was heated to 60-65° C., the phases were separated and the organic phase was washed with 2 more portions of water (30.0 mL). The organic phase was filtered on active charcoal, the filter washed with toluene (60.0 mL). The filtrate was concentrated under reduced pressure to a volume of ca. 120 mL, heated to reflux and 1-propanol (0.8 mL) was added to obtain a solution. The solution was cooled to 0-5° C. within 4-6 hours, stirred at 0-5° C. for 1 hour. The precipitate was filtered off, washed with toluene (30 mL) and dried under reduced pressure at 70-80° C. to afford tert-butyl 7-[2-(2,8-dimethylimidazo[1,2-b]pyridazin-6-yl)-4-oxo-pyrido[1,2-a]pyrimidin-7-yl]-4,7-diazaspiro[2.5]octane-4-carboxylate (7.7 g, 80.8%) as a yellowish solid.

EXAMPLE 13

7-(4,7-diazaspiro[2.5]octan-7-yl)-2-(2,8-dimethylimidazo[1,2-b]pyridazin-6-yl)pyrido[1,2-a]pyrimidin-4-one Di-hydrochloride Salt

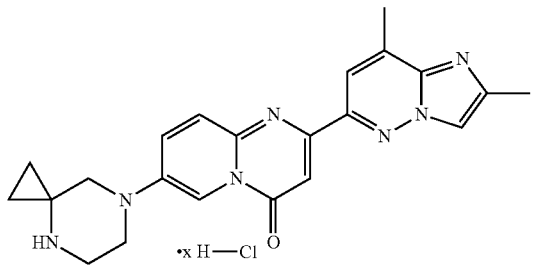

To prepare a solution of HCl in in 1-propyl acetate/1-propanol, acetyl chloride (15.8 g, 199 mmol) was slowly added to a mixture of 1-propyl acetate (60 mL) and 1-propanol (30 mL) at 0° C., and stirring was pursued for an additional 2 hours at room temperature.

tert-Butyl 7-[2-(2,8-dimethylimidazo[1,2-b]pyridazin-6-yl)-4-oxo-pyrido[1,2-a]pyrimidin-7-yl]-4,7-diazaspiro[2.5]octane-4-carboxylate (20 g, 39.9 mmol) was suspended in 1-propyl acetate (60 mL) and 1-propanol (30 mL) at room temperature and the HCl solution in 1-propyl acetate and 1-propanol was added. The reaction mixture was heated within 3 hours to 70° C. and stirred 16 hours at this temperature, then cooled to 20° C. The precipitate was filtered off, washed with 1-propyl acetate (50 mL) in several portions and dried under vacuum at 55° C. to afford 7-(4,7-diazaspiro[2.5]octan-7-yl)-2-(2,8-dimethylimidazo[1,2-b]pyridazin-6-yl)pyrido[1,2-a]pyrimidin-4-one hydrochloride salt (18.8 g, 99%) as yellow crystals.

¹H-NMR (CDCl₃, 600 MHz): 8.34 (s, 1H); 8.22 (s, 1H); 8.05 (s, 1H); 8.01 (dd, 1H); 7.80 (d, 1H); 7.16 (s, 1H); 3.71-3.67 (m, 2H); 3.64-3.59 (m, 2H); 3.52 (s, 2H); 2.69 (s, 3H); 2.54 (s, 3H); 1.23-1.20 (m, 2H); 1.14-1.08 (m, 2H); LCMS: 402.20 (M+H⁺)

EXAMPLE 14

7-(4,7-diazaspiro[2.5]octan-7-yl)-2-(2,8-dimethylimidazo[1,2-b]pyridazin-6-yl)pyrido[1,2-a]pyrimidin-4-one

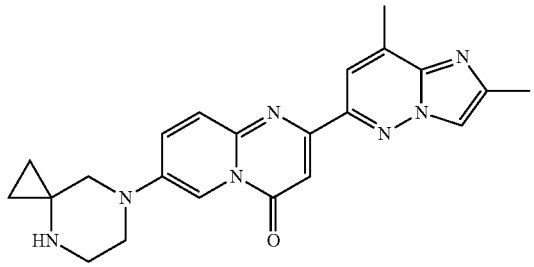 [SMILES: Cc1cn2nc(-c3cc(=O)n4cc(N5CCNC6(CC6)C5)ccc4n3)cc(C)c2n1]

To a suspension of tert-butyl 7-[2-(2,8-dimethylimidazo[1,2-b]pyridazin-6-yl)-4-oxo-pyrido[1,2-a]pyrimidin-7-yl]-4,7-diazaspiro[2.5]octane-4-carboxylate (25 g, 50 mmol) in 1-propyl acetate (375 mL) was added a solution of HCl in 1-propanol (prepared by adding slowly at 5° C. acetyl chloride (18.0 mL) to 1-propanol (37.6 mL) and stirring 1 hour at room temperature). The stirred suspension was heated to 75° C. within 10 hours and stirred a further 5 hours at 75° C. Water (160.0 mL) was added and the phases were separated at 75° C. Aqueous sodium hydroxide 32% (27.8 mL) was added to the aqueous phase. The suspension obtained was cooled to room temperature within 5 hours and stirred one hour at room temperature. The precipitate was filtered off, washed with water (100.0 mL) and dried under reduced pressure at 50° C. for 18 hours to afford 7-(4,7-diazaspiro[2.5]octan-7-yl)-2-(2,8-dimethylimidazo[1,2-b]pyridazin-6-yl)pyrido[1,2-a]pyrimidin-4-one (19.7 g, 98.3%) as yellow crystals.

$^1$H-NMR (CDCl$_3$, 600 MHz): 8.45 (d, 1H); 7.92 (d, 1H); 7.80 (s, 1H); 7.75-7.71 (m, 1H); 7.71-7.67 (m, 1H); 7.37 (s, 1H); 3.31-3.24 (m, 2H); 3.22-3.16 (m, 2H); 3.09 (s, 2H); 2.73 (s, 3H); 2.55 (s, 3H); 0.82-0.76 (m, 2H); 0.71-0.63 (m, 2H); LCMS: 402.20 (M+H$^+$)

EXAMPLE 15

7-(4,7-diazaspiro[2.5]octan-7-yl)-2-(2,8-dimethyl-imidazo[1,2-b]pyridazin-6-yl)pyrido[1,2-a]pyrimi-din-4-one

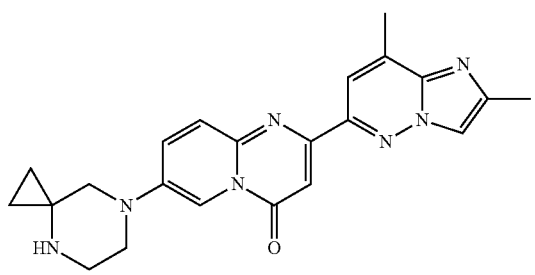 [SMILES: Cc1cn2nc(-c3cc(=O)n4cc(N5CCNC6(CC6)C5)ccc4n3)cc(C)c2n1]

A suspension of tert-butyl 7-[2-(2,8-dimethylimidazo[1,2-b]pyridazin-6-yl)-4-oxo-pyrido[1,2-a]pyrimidin-7-yl]-4,7-diazaspiro[2.5]octane-4-carboxylate (13.5 g, 26.9 mmol) in toluene (237.0 g) was stirred at 75° C. and a 21.9% solution of HCl in 1-propanol (21.4 g, 134.5 mmol) was added within 2.5 hours. The reaction mixture was stirred further at 75° C. until complete conversion. The reaction mixture was cooled to 20-25° C. Water (70 g) was added. The biphasic mixture was stirred another 10 minutes at 20-25° C. and the phases were separated. The organic phase was extracted with water (17 g) twice and the combined aqueous phases were added into mixture of aqueous sodium hydroxide 28% (15.0 g) and water (45.0 g). The suspension obtained was cooled to 20° C. The precipitate was filtered off, washed with water (25 g) three times and dried under reduced pressure at 60° C. to afford 7-(4,7-diazaspiro[2.5]octan-7-yl)-2-(2,8-dimethylimidazo[1,2-b]pyridazin-6-yl)pyrido[1,2-a]pyrimidin-4-one (9.5 g, 95.1%) as yellow crystals.

EXAMPLE 16

4-bromo-6-chloro-pyridazin-3-amine

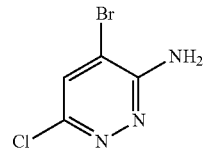

3-amino-6-chloropyridazine (20 g, 154 mmol), sodium bicarbonate (25.9 g, 309 mmol) and methanol (158 g) were charged in a reaction vessel and cooled to 0-10° C. Bromine (34.5 g, 216 mmol) was added drop wise and the reaction mixture was stirred 3 days at room temperature. 10% Aqueous sodium sulfate was added. The suspension was filtered off. The filtrate was washed with ethyl acetate (300 mL) twice. The combined organic layers were dried and evaporated. A suspension of the residue in methanol (50 mL) was heated to reflux, water (120 mL) was added and the suspension was stirred 16 hours at room temperature. The precipitate was filtered off and dried. The residue was suspended in n-heptane (50 mL), stirred 2 hours at room temperature, filtered off and dried to afford 4-bromo-6-chloro-pyridazin-3-amine (14.5 g, 46.2%) as a light brown solid.

$^1$H-NMR (CDCl$_3$, 600 MHz): 7.55 (s, 1H); 5.83-4.89 (m, 2H); LCMS: 209.93 (M+H$^+$)

EXAMPLE 17

4-bromo-6-chloro-pyridazin-3-amine

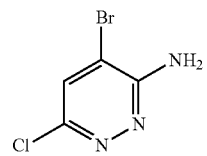

3-amino-6-chloropyridazine (50 g, 360 mmol), acetic acid (5.8 g, 96.5 mmol), sodium acetate (28.7 g, 289.5 mmol) and methanol (395 g) were charged in a reaction vessel and heated to 25-35° C. Dibromodimethylhydatoin (66.0 g, 231.6 mmol) was added in several portions and the reaction mixture was stirred 3 hours at 30° C. Completion is checked by IPC and if the conversion is incomplete, dibromodimethylhydantoin is added (5.5 g). At reaction completion, 38% aqueous sodium sulfate (77.2 mmol NaHSO$_3$) was added slowly. The suspension was concentrated under reduced pressure and water (500 g) was added slowly at 45° C., then 30% aqueous sodium hydroxide (31.5 g, 231.6 mmol NaOH) was added at 20° C. to adjust pH to 7-8. The precipitate was filtered off, washed with water and dried under reduced pressure to afford 4-bromo-6-chloro-pyridazin-3-amine (50.2 g, 62.5%) as a grey solid.

EXAMPLE 18

6-chloro-4-methyl-pyridazin-3-amine

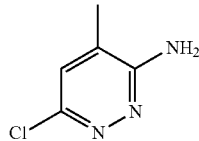

4-bromo-6-chloro-pyridazin-3-amine (3.0 g, 14.4 mmol) and tetrakis(triphenylphosphine)palladium (1666 mg, 144 µmol) were suspended in THF (13.2 g) and a solution of zinc chloride in Me-THF (2.0 M, 9 mL, 18 mmol) was added. The reaction mixture was cooled to −5° C. and methyllithium in diethoxymethane (3.1 M, 11.6 mL, 36 mmol) was added. The reaction mixture was stirred at 45° C. for 4 hours. Sodium sulfate decahydrate (11.7 g, 36 mmol) was added at room temperature, the mixture was stirred 1.5 hours at 60° C., diluted with water (100 mL) and after 30 minutes the precipitate was filtered off. The precipitate was dissolved in aqueous HCl 2M (100 mL) and ethyl acetate (140 mL). The biphasic system was filtered, the phases were separated and the pH of the water layer adjusted to 7 with aqueous NaOH 32% (18 mL). The precipitate was filtered and dried. The solid obtained was digested twice in methanol (20 mL) at room temperature. The two filtrates were combined, evaporated and dried under high vacuum to afford 6-chloro-4-methyl-pyridazin-3-amine (1.2 g, 58.1%) as a red solid.

$^1$H-NMR (CDCl$_3$, 600 MHz): 7.09 (d, 1H); 4.90 (br s, 2H), 2.17 (d, 3H)

EXAMPLE 19

6-chloro-4-methyl-pyridazin-3-amine

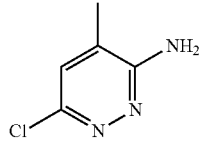

4-bromo-6-chloro-pyridazin-3-amine (30.02 g, 143 mmol) and THF (180 mL) were charged into a reaction vessel. Methylmagnesium chloride (22% in THF, 50.0 mL, 1.03 eq.) was added at 20° C. over 60 minutes, followed by zinc chloride in Me-THF (25%, 37 mL, 0.50 eq.) and palladium tetrakis(triphenyphosphine) (1.66 g, 1 mol %). The reaction mixture was heated to 50° C. and methylmagnesium chloride (22% in THF, 81 mL, 1.7 eq.) was added slowly. The reaction mixture was stirred at 50° C. until complete conversion, then at 10° C. for 14.5 hours and poured into a mixture of water (90 g), aqueous HCl 33% (52.5 g) and toluene (150 mL) maintained at 20-30° C. The aqueous phase was separated and the organic phase was extracted with a solution of aqueous HCl 33% (2.0 g) and water (45 g). The aqueous layers were combined and washed with toluene (30 mL) twice and the pH was adjusted by addition of 25% aqueous ammonia solution. When a pH of 2.4 was reached, seeding crystals were added, the mixture was stirred further for 15 minutes and thereafter the pH was brought to 4.0. The suspension was stirred at 20° C. for 2 hours, the precipitate was filtered off, washed with water (20 mL) three times to afford crude 6-chloro-4-methyl-pyridazin-3-amine (29 g) as a brown solid.

29 g crude product was transferred to a reaction vessel and methanol (20 mL) was added. The mixture was refluxed for 30 minutes and 12 g water was added. The solution was cooled to 0° C. and stirred for 2 hours at this temperature. The precipitate was filtered off, washed with water three times and dried under reduced pressure at 40° C. to afford purified 6-chloro-4-methyl-pyridazin-3-amine (13.8 g, 66%) as a light brown solid.

Alternative Purification:

50 g crude 6-chloro-4-methyl-pyridazin-3-amine were dissolved in methanol (250 mL) and active charcoal (4.0 g) and diatomaceous earth (2.5 g) were added. The suspension was stirred at 45° C. for 1 hour, cooled to 30° C. and potassium hydrogenophosphate (2.1 g) was added. The suspension was stirred at 30° C. for another 90 minutes, filtered and the precipitate washed with methanol (100 mL). The filtrate was concentrated to a residual volume of 175 mL and water (120 mL) was added. The resulting suspension was heated to reflux affording a solution which was cooled to 20° C. resulting in a suspension. The precipitate was filtered off, washed with water (90 mL) and dried under reduced pressure to afford pure 6-chloro-4-methyl-pyridazin-3-amine (38 g, 76%) as a light yellow solid.

EXAMPLE 20

6-chloro-2,8-dimethyl-imidazo[1,2-b]pyridazine

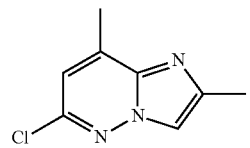

6-chloro-4-methyl-pyridazin-3-amine (70.95 kg, 494.2 mol), sodium bromide (35 kg, 345.9 mol), isopropyl acetate (611 kg), isopropanol (28 kg and water (35 kg) were charged into a reaction vessel. The reaction mixture was stirred at 80-85° C. for 8 hours. Isopropyl acetate (310 kg) and water (420 kg) were added. 30% Aqueous NaOH was added at 45-55° C. and the system was stirred for 2 hours. The phases were separated at 25-35° C. The organic layer was washed with water (370 kg), filtered on diatomite (7 kg) and the filter washed with isopropyl acetate (35 kg). The organic phase was extracted with two portions of 5.4% aqueous sulfuric acid (910 kg followed by 579 kg). The combined aqueous phases were basified with 30% aqueous NaOH (158 kg). The suspension was stirred 2 hours at 15-25° C. The precipitate was isolated by centrifugation in three portions, each washed with water (31 kg). The wet solid was dissolved in isopropyl acetate (980 kg) at 25-35° C., the solution washed with water (210 kg), three times. The organic phase was treated with active charcoal for 12 hours at 45-50° C., concentrated to ca. 300 kg and heated to 70-80° C. to obtain a clear solution. This solution was cooled to 50-60° C., stirred at this temperature for 1 hour, n-heptane (378 kg) was added and stirring was pursued for 1 hour. The mixture was cooled to −10-−5° C. and stirred for another 3 hours. The precipitate was isolated by centrifuging, washed with n-heptane (33 kg) and dried under reduced pressure at 30-50° C.

for 15 hours to afford 67.4 kg (76%) 6-chloro-2,8-dimethyl-imidazo[1,2-b]pyridazine as an off-white solid.

$^1$H-NMR (CDCl$_3$, 600 MHz): 7.67 (s, 1H); 6.86 (s, 1H); 2.65 (s, 3H), 2.50 (s, 3H)

What is claimed is:

1. A process for the preparation of a compound of formula (II)

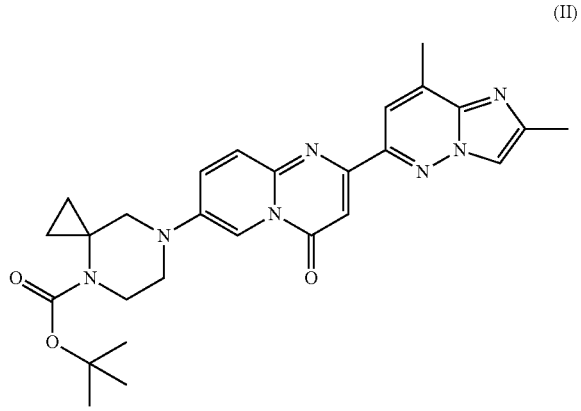 [SMILES: Cc1cn2nc(-c3cc(=O)n4cc(N5CCN(C(=O)OC(C)(C)C)C6(CC6)C5)ccc4n3)cc(C)c2n1]

(II)

which comprises reacting a compound of formula (III)

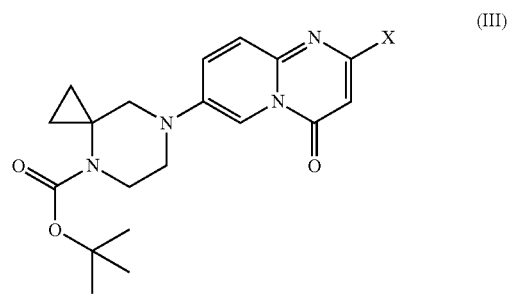

(III)

with a compound of formula (III'), (III$_a$') or (III$_b$')

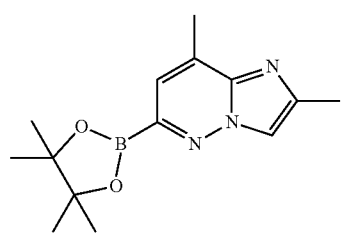

(III$_a$')

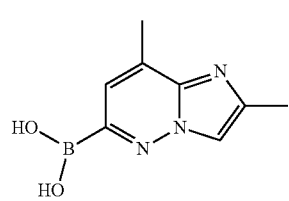

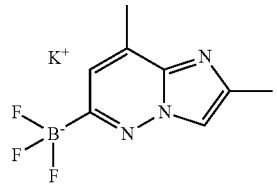

(III$_b$')

in the presence of a palladium catalyst or nickel catalyst to form the compound of formula (II), wherein X is selected from an alkyl, aryl sulfonate, fluorinated alkyl, fluorinated aryl sulfonate and halide.

2. The process of claim 1, wherein the compound of formula (III) is reacted with the compound of formula (III'), (III$_a$') or (III$_b$') in presence of a palladium catalyst.

3. The process of claim 1, wherein X is selected from the group consisting of pTolSO$_3$—, CH$_3$SO$_3$—, phenyl-SO$_3$—, CF$_3$SO$_3$—, nonaflate, Cl, Br, and I.

4. The process of claim 1, wherein said process is carried out in the presence of a base.

5. The process of claim 4, wherein the base is selected from the group consisting of Na$_2$CO$_3$, K$_2$CO$_3$, Cs$_2$CO$_3$, KOAc and KOtBu.

6. The process of claim 5, wherein the base is K$_2$CO$_3$.

7. The process of claim 4, wherein said process is carried out in the presence of a palladium catalyst and base.

8. The process of claim 1, wherein the compound of formula (III) is reacted with the compound of formula (III').

9. The process of claim 8, wherein said process further comprises reacting a compound having formula

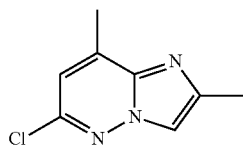

with bis(pinacolato)diboron to obtain the compound of formula (III'):

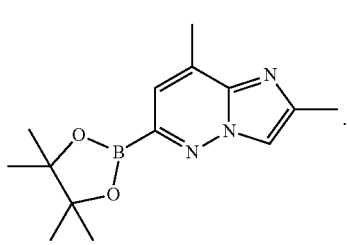

(III')

10. The process of claim 1, wherein said process further comprises
reacting a compound of formula (IV)

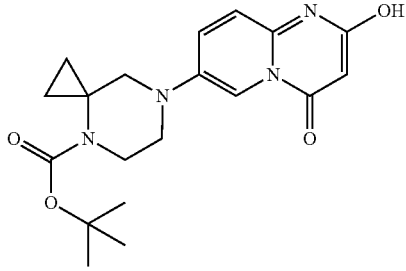

with
tosyl chloride when X is pTol—SO₃—,
methanesulfonyl chloride when X is CH₃SO₃—,
triflyl chloride when X is CF₃SO₃— or
phenylsulfonylchloride when X is phenyl—SO₃—,
in the presence of a base; or with
POCl₃ when X is Cl,
POBr₃ when X is Br, or
Ph₃PI₂ or POCl₃ followed by NaI or CuI, when X is I
for the preparation of the compound of formula (III)

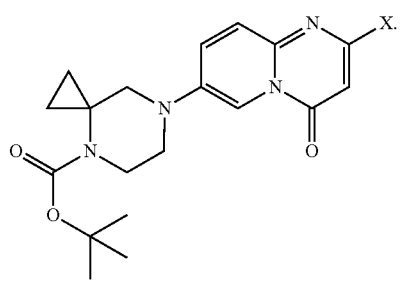

11. The process of claim 10, wherein the base is an organic base or basic alkali metal salts.

12. The process of claim 11, wherein the base is nitrogen-containing heterocycle, tertiary amine or basic alkali metal salts.

13. The process of claim 12, wherein the base is a tertiary amine.

14. The process of claim 10, wherein said process further comprises
reacting a compound of formula (V)

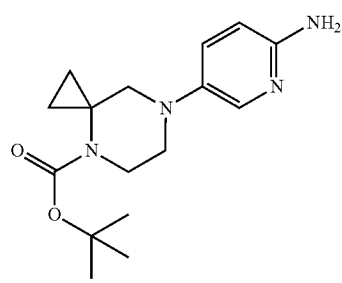

with di-tert-butyl malonate for the preparation of the compound of formula (IV)

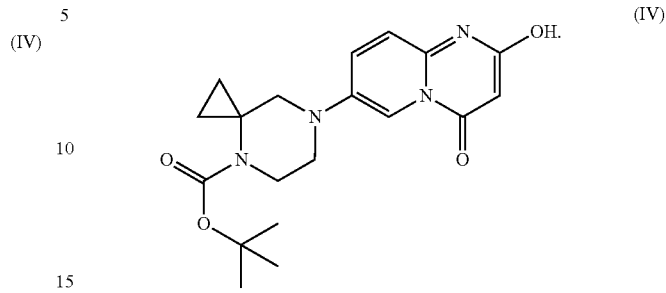

15. The process of claim 14, wherein said process is carried out in the presence of xylene, dichlorobenzene, toluene or anisole.

16. The process according to claim 15, wherein said process is carried out in the presence of anisole.

17. The process of claim 14, said process further comprising reducing a compound of formula (VI)

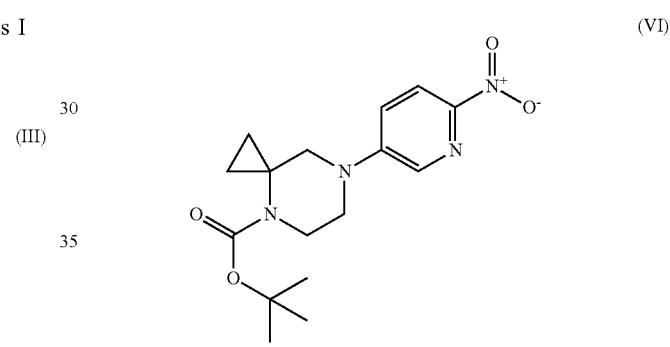

to provide the compound of formula (V)

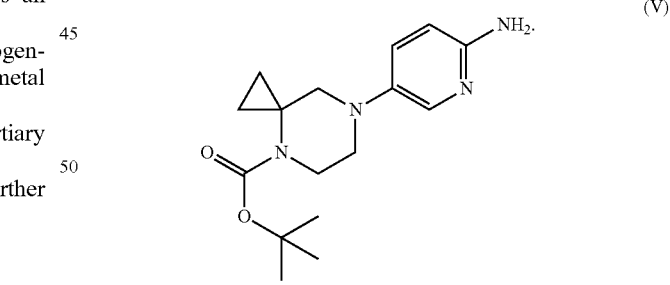

18. The process of claim 17, wherein reducing a compound of formula (VI) comprises reacting said compound with a transition metal hydrogenation catalyst to obtain the compound of formula (V).

19. The process according to claim 18, wherein the transition metal hydrogenation catalyst is selected from the group consisting of a Raney catalyst, Pd/C, Pd(OH)₂/C, Au/TiO₂, Rh/C, Ru/Al₂O₃, Ir/CaCO₃, Pt-V/C, Pt/C and combinations thereof.

20. The process according to claim 19, wherein the transition metal hydrogenation catalyst is Pt-V/C.

21. The process according to claim 20, wherein the transition metal hydrogenation catalyst is Pt 1% and V 2% on activated carbon.

22. The process of claim 17, said process further comprising reacting a compound of formula (VII)

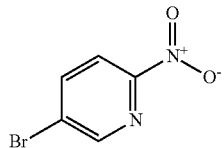
(VII)

with a compound of formula (VIII)

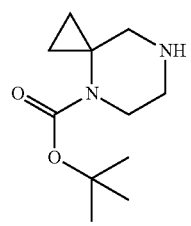
(VIII)

or a salt thereof for the preparation of the compound of formula (VI)

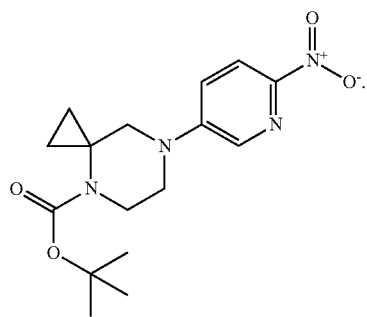
(VI)

23. The process of claim 22, wherein the salt is an oxalate salt.

24. A process for the preparation of a compound of formula (I)

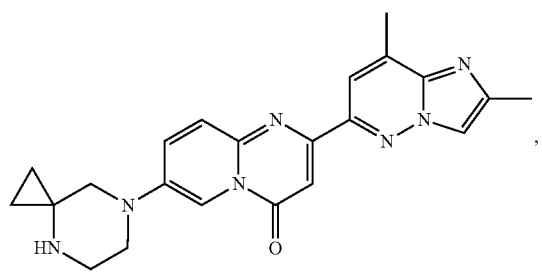
(I)

said process comprising preparing a compound of formula (II) comprising

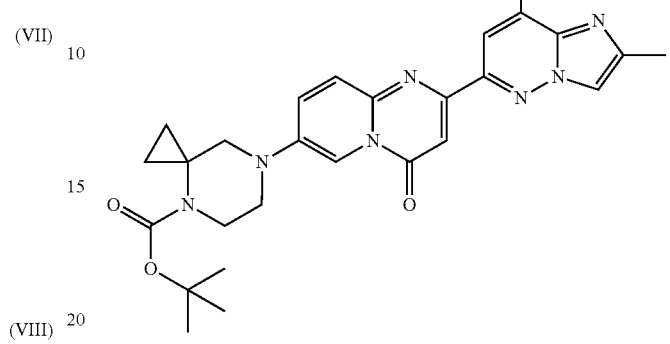
(II)

reacting a compound of formula (III)

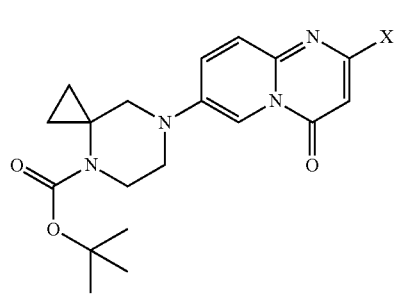
(III)

with a compound of formula (III'), (III$_a$') or (III$_b$')

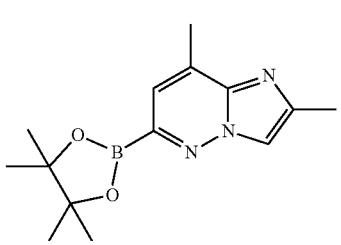
(III')

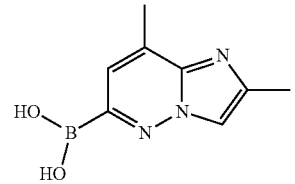
(III$_a$')

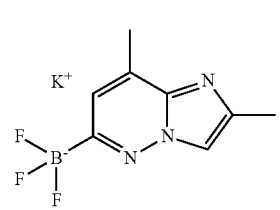
(III$_b$')

in the presence of a palladium catalyst or nickel catalyst to form the compound of formula (II), wherein X is selected from an alkyl, aryl sulfonate, fluorinated alkyl, fluorinated aryl sulfonate and halide; and reacting the compound of formula (II)

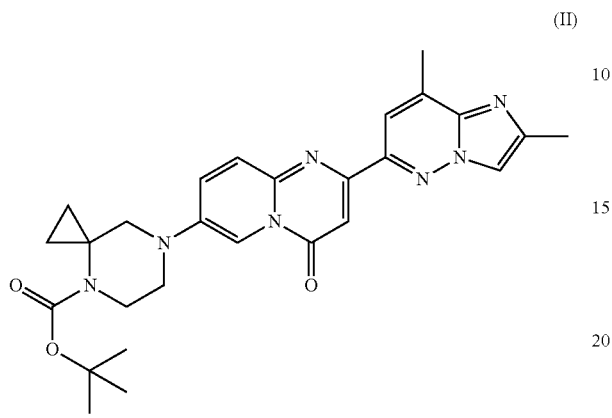

(II)

with a strong acid for the preparation of a compound of formula (I) or a pharmaceutically acceptable salt thereof.

25. The process of claim 24, wherein the strong acid is HCl.

26. The process of claim 25, wherein the HCl is made in situ with 1-propanol and acetyl chloride.

* * * * *